US011850256B2

(12) United States Patent
Burke et al.

(10) Patent No.: US 11,850,256 B2
(45) Date of Patent: Dec. 26, 2023

(54) SMALL MOLECULE-MEDIATED RESTORATION OF AIRWAY SURFACE PHYSIOLOGY IN HUMAN CYSTIC FIBROSIS LUNG EPITHELIA

(71) Applicant: The Board of Trustees of the University of Illinois, Urbana, IL (US)

(72) Inventors: Martin D. Burke, Champaign, IL (US); Katrina A. Muraglia, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 102 days.

(21) Appl. No.: 17/335,803

(22) Filed: Jun. 1, 2021

(65) Prior Publication Data

US 2021/0393661 A1    Dec. 23, 2021

Related U.S. Application Data

(62) Division of application No. 16/091,599, filed as application No. PCT/US2017/026806 on Apr. 10, 2017, now abandoned.

(60) Provisional application No. 62/320,795, filed on Apr. 11, 2016, provisional application No. 62/320,111, filed on Apr. 8, 2016.

(51) Int. Cl.
| | |
|---|---|
| *A61K 31/7048* | (2006.01) |
| *A61K 9/00* | (2006.01) |
| *A61K 31/575* | (2006.01) |
| *A61K 47/28* | (2006.01) |
| *C07H 17/08* | (2006.01) |
| *A61P 11/10* | (2006.01) |

(52) U.S. Cl.
CPC .......... *A61K 31/7048* (2013.01); *A61K 9/007* (2013.01); *A61K 9/0019* (2013.01); *A61K 9/0073* (2013.01); *A61K 31/575* (2013.01); *A61K 47/28* (2013.01); *A61P 11/10* (2018.01); *C07H 17/08* (2013.01)

(58) Field of Classification Search
CPC .. A61K 31/7048; A61K 9/0019; A61K 9/007; A61K 9/0073; A61K 31/575; A61K 47/28; A61P 11/10; C07H 17/08
USPC .......................................................... 514/31
See application file for complete search history.

(56) References Cited

U.S. PATENT DOCUMENTS

| | | | |
|---|---|---|---|
| 5,049,389 | A | 9/1991 | Radhakrishnan |
| 5,880,101 | A | 3/1999 | Stankov |
| 8,883,748 | B2 | 11/2014 | Verma et al. |
| 2009/0220599 | A1 | 9/2009 | Tsai et al. |
| 2010/0210575 | A1 | 8/2010 | Kwon et al. |
| 2012/0015897 | A1 | 1/2012 | Verma et al. |
| 2019/0083517 | A1 | 3/2019 | Burke et al. |
| 2021/0393661 | A1 | 12/2021 | Burke et al. |

FOREIGN PATENT DOCUMENTS

| | | |
|---|---|---|
| WO | WO-2005/120497 A2 | 12/2005 |
| WO | WO-2008/127358 A2 | 10/2008 |
| WO | WO-2015/054148 A1 | 4/2015 |
| WO | WO-2016/073462 A1 | 5/2016 |
| WO | WO-2017/177228 A1 | 10/2017 |

OTHER PUBLICATIONS

Glossary of medical education terms, Institute of International Medical Education. http://www.iime.org/glossary.htm Accessed in Mar. 2013. (Year: 2013).*
Misra et al. Recent advances in liposomal dry powder formulations: preparation and evaluation. Expert Opin. Drug Deliv. (2009) 6 (1):71-89. (Year: 2009).*
Proesmans et al. Use of Nebulized Amphotericin B in the Treatment of Allergic Bronchopulmonary Aspergillosis in Cystic Fibrosis. International Journal of Pediatrics, vol. 2010, Article ID 376287, 9 pages. (Year: 2010).*
Chuealee R. Amphotericin B Incorporated in Liquid Crystals for Lung Fungal Infection Treatment. A Thesis, Doctor of Philosophy in Pharmaceutical Sciences, Prince of Songkla University, 2009. (Year: 2009).*
Anderson et al., "Amphotericin Forms an Extramembranous and Fungicidal Sterol Sponge," Nat Chem Biol, 10(5): 400-406 (2014).
Chuealee, "Amphotericin B incorporated in liquid crystals for fungal infection treatment," A Thesis, Prince of Songkia University, (2009).
Cioffi et al., "Restored Physiology in Protein-Deficient Yeast by a Small Molecule Channel," Journal of The American Chemical Society, 137:10096-10099 (2015).
Cioffi et al., "Supporting Information for: Restored physiology in protein-deficient yeast by a small molecule channel," S1-S14 (2015).
Extended European Search Report for EP Application No. EP 17779973 dated Nov. 18, 2019.
Gray et al., "Amphotericin Primarily Kills Yeast by Simply Binding Ergosterol," PNAS, 109(7): 2234-2239 (2012).
International Preliminary Report on Patentability for International Application No. PCT/US2017/026806 dated Oct. 9, 2018.
International Search Report and Written Opinion for International Application No. PCT/US2017/026806 dated Jun. 28, 2017.
Extended European Search Report for EP Application No. 17779973.1 dated Mar. 9, 2023.
Proesmans et al., "Use of Nebulized Amphotericin B in the Treatment of Allergic Bronchopulmonary Aspergillosis in Cystic Fibrosis", International Journal of Pediatrics, vol. 2010, 1 2010, pp. 1-9, XP055692923.
Stone et al., "Liposomal Amphotericin B (AmBisome ): A Review of the Pharmacokinetics, Pharmacodynamics, Clinical Experience and Future Directions", Drugs, vol. 76, No. 4, Mar. 1, 2016, pp. 485-500, XP093027684.

* cited by examiner

*Primary Examiner* — Yih-Horng Shiao
(74) *Attorney, Agent, or Firm* — Foley Hoag LLP; Dana M. Gordon; Benjamin A. Vaughan

(57) ABSTRACT

Provided herein are complexes comprising amphotericin B (AmB) or derivatives and sterols. Also provided herein are methods of treating cystic fibrosis using AmB or complexes comprising AmB or derivatives and sterols.

16 Claims, 25 Drawing Sheets

Amphotericin B (AmB)

C35deOAmB

C3deOAmB

| Patient # | Genotype | Mutation Class |
|---|---|---|
| 1 | ΔF508/ΔF508 | II/II |
| 2 | ΔF508/ΔF508 | II/II |
| 3 | ΔF508/ΔF508 | II/II |
| 4 | ΔF508/ΔF508 | II/II |
| 5 | ΔF508/ΔF508 | II/II |
| 6 | R553X/E60X | I/I |
| 7 | ΔF508/1717-1G→A | II/I |
| 8 | ΔF508/c.2052dupA | II/U |
| 9 | D239G/V520F | U/III |

SMALL MOLECULE-MEDIATED RESTORATION OF AIRWAY SURFACE PHYSIOLOGY IN HUMAN CYSTIC FIBROSIS LUNG EPITHELIA

RELATED APPLICATIONS

This application is a divisional of U.S. patent application Ser. No. 16/091,599, filed Oct. 5, 2018; which is a § 371 national stage application based on Patent Cooperation Treaty Application serial number PCT/US2017/026806, filed Apr. 10, 2017; which claims the benefit of priority to U.S. Provisional Patent Application Ser. No. 62/320,111, filed Apr. 8, 2016; and U.S. Provisional Patent Application Ser. No. 62/320,795, filed Apr. 11, 2016.

GOVERNMENT SUPPORT

This invention was made with government support under Grant No. GM080436, awarded by the National Institutes of Health. The government has certain rights in the invention.

BACKGROUND OF THE INVENTION

Cystic fibrosis is an autosomal recessive genetic disease that substantially shortens lifespan in affected individuals. It occurs in 1 in 3,000 live births, and is caused by mutations in the CFTR gene encoding cystic fibrosis transmembrane conductance regulator (CFTR), a membrane-expressed anion channel protein in vertebrates. The disease is most often characterized by chronic and potentially fatal respiratory infections, and for most patients with cystic fibrosis, only symptomatic treatments are available. The median survival of patients is only 33 years.

CFTR is an ABC transporter-class ion channel that conducts chloride ions across epithelial cell membranes. Mutations of the CFTR gene affecting chloride ion channel function lead to dysregulation of epithelial fluid transport in the lung, pancreas and other organs, resulting in cystic fibrosis. Complications include thickened mucus in the lungs with frequent respiratory infections, and pancreatic insufficiency giving rise to malnutrition and diabetes. These conditions lead to chronic disability and reduced life expectancy. In male patients the progressive obstruction and destruction of the developing vas deferens and epididymis appear to result from abnormal intraluminal secretions, causing congenital absence of the vas deferens and male infertility.

CFTR functions as a cAMP-activated ATP-gated anion channel, increasing the conductance for certain anions (e.g., Cl$^-$) to flow down their electrochemical gradient. ATP-driven conformational changes in CFTR open and close a gate to allow transmembrane flow of anions down their electrochemical gradient. This function is in contrast to other ABC proteins, in which ATP-driven conformational changes fuel uphill substrate transport across cellular membranes. Essentially, CFTR is an ion channel that evolved as a "broken" ABC transporter that leaks when in the open conformation.

Mutations of the CFTR gene affecting anion channel function lead to dysregulation of epithelial ion and fluid transport, thickened mucus, and frequent respiratory infections in the lung, primarily causing the life-shortening pathophysiology associated with cystic fibrosis. CFTR is found in the epithelial cells of many organs including the lung, liver, pancreas, digestive tract, reproductive tract, and skin. In the lung, the protein ion channel moves bicarbonate and chloride ions out of an epithelial cell to the apical airway surface liquid (ASL). This maintains proper ASL pH, viscosity, and activity of pH-sensitive antimicrobial proteins. Changes in the ASL due to CFTR dysfunction impair the clearance and killing of bacteria, leaving patients vulnerable to the chronic airway infections that are the primary driver of morbidity and mortality.

A compelling need exists for effective treatments of cystic fibrosis.

SUMMARY OF THE INVENTION

An aspect of the invention is a complex, comprising (i) amphotericin B (AmB), or a pharmaceutically acceptable salt or hydrate thereof, and (ii) cholesterol. This and similar complexes can be formed as disclosed herein, and they can be assayed by various methods, such as the method disclosed in the Examples. Anderson T M et al. (2014) *Nat Chem Biol* 10(5):404-406.

An aspect of the invention is a composition, comprising (i) amphotericin B (AmB), or a pharmaceutically acceptable salt or hydrate thereof, and (ii) cholesterol, wherein the molar ratio of AmB to cholesterol is greater than 1:2.4 (e.g., 1:2 or 1:1) or in the range from 1:2.6 to about 1:50.

An aspect of the invention is a composition, comprising (i) amphotericin B (AmB), or a pharmaceutically acceptable salt or hydrate thereof, and (ii) cholesterol, wherein the molar ratio of AmB to cholesterol is in the range from 1:2.6 to about 1:50.

An aspect of the invention is a composition, comprising (i) amphotericin B (AmB), or a pharmaceutically acceptable salt or hydrate thereof, and (ii) cholesterol, wherein the molar ratio of AmB to cholesterol is in the range from about 1:3 to about 1:15.

An aspect of the invention is a complex, comprising (i) C3-deoxy amphotericin B (C3deOAmB), or a pharmaceutically acceptable salt or hydrate thereof, and (ii) cholesterol.

An aspect of the invention is a composition, comprising (i) C3-deoxy amphotericin B (C3deOAmB), or a pharmaceutically acceptable salt or hydrate thereof, and (ii) cholesterol, wherein the molar ratio of C3deOAmB to cholesterol is in the range from 1:2.6 to about 1:50.

An aspect of the invention is a composition, comprising (i) C3-deoxy amphotericin B (C3deOAmB), or a pharmaceutically acceptable salt or hydrate thereof, and (ii) cholesterol, wherein the molar ratio of C3deOAmB to cholesterol is in the range from about 1:3 to about 1:15.

An aspect of the invention is a method of treating cystic fibrosis, comprising administering to a subject in need thereof a therapeutically effective amount of a complex comprising (i) amphotericin B (AmB), or a pharmaceutically acceptable salt or hydrate thereof, and (ii) cholesterol, thereby treating the cystic fibrosis.

An aspect of the invention is a method of treating cystic fibrosis, comprising administering to a subject in need thereof a therapeutically effective amount of a composition comprising (i) amphotericin B (AmB), or a pharmaceutically acceptable salt or hydrate thereof, and (ii) cholesterol, thereby treating the cystic fibrosis.

An aspect of the invention is a method of treating cystic fibrosis, comprising administering to a subject in need thereof a therapeutically effective amount of a complex comprising (i) C3-deoxy amphotericin B (C3deOAmB), or a pharmaceutically acceptable salt or hydrate thereof, and (ii) cholesterol, thereby treating the cystic fibrosis.

An aspect of the invention is a method of treating cystic fibrosis, comprising administering to a subject in need thereof a therapeutically effective amount of a composition comprising (i) C3-deoxy amphotericin B (C3deOAmB), or a pharmaceutically acceptable salt or hydrate thereof, and (ii) cholesterol, thereby treating the cystic fibrosis.

An aspect of the invention is a method of increasing the pH of airway surface liquid in a subject having cystic fibrosis, comprising administering to a subject having cystic fibrosis a therapeutically effective amount of a complex comprising (i) amphotericin B (AmB), or a pharmaceutically acceptable salt or hydrate thereof, and (ii) cholesterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) amphotericin B (AmB), or a pharmaceutically acceptable salt or hydrate thereof, and (ii) cholesterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a complex comprising (i) C3-deoxy amphotericin B (C3deOAmB), or a pharmaceutically acceptable salt or hydrate thereof, and (ii) cholesterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) C3-deoxy amphotericin B (C3deOAmB), or a pharmaceutically acceptable salt or hydrate thereof, and (ii) cholesterol, thereby increasing the pH of airway surface liquid in the subject having cystic fibrosis.

In each of the preceding aspects of the invention, in certain embodiments the AmB or C3deOAmB and the cholesterol are present as a complex.

In an aspect, provided herein is a method of treating cystic fibrosis, comprising administering to a subject in need thereof a therapeutically effective amount of a composition comprising amphotericin B (AmB) or a pharmaceutically acceptable salt or hydrate thereof, thereby treating the cystic fibrosis.

In an aspect, provided herein is a method of increasing the pH of airway surface liquid in a subject having cystic fibrosis, comprising administering to a subject having cystic fibrosis a therapeutically effective amount of a composition comprising amphotericin B (AmB) or a pharmaceutically acceptable salt or hydrate thereof, thereby increasing the pH of airway surface liquid in the subject having cystic fibrosis.

In an aspect, provided herein is a method of increasing the bicarbonate in airway surface liquid in a subject having cystic fibrosis, comprising administering to a subject having cystic fibrosis a therapeutically effective amount of amphotericin B (AmB), or a pharmaceutically acceptable salt or hydrate thereof, thereby increasing the bicarbonate of airway surface liquid in the subject having cystic fibrosis.

DETAILED DESCRIPTION OF THE INVENTION

Loss of functional CFTR in cystic fibrosis results in two major effects in the lung. First, the reduced secretion of $Cl^-$ and $HCO_3^-$ at the apical surface of pulmonary epithelia alters mucus properties, making mucus more viscous and thereby impeding normal airway clearance mechanisms. Additionally, in humans and pigs lacking CFTR unchecked $H^+$ secretion by the nongastric $H^+/K^+$ adenosine triphosphatase (ATP12A) acidifies airway surface liquid (ASL), which impairs airway host defenses. In contrast, airways in CF mice express little ATP12A and secrete minimal $H^+$; consequently, airway surface liquid in CF and non-CF mice have similar pH. Pezzulo A A et al. (2012) Nature 487: 109-113; Shah V S et al. (2016) Science 351: 503-507.

In some embodiments, small molecule ion channels introduced into CF epithelia can restore physiologic features of ASL in CF lung epithelia via proton absorption, bicarbonate secretion, or both. Such a molecular prosthetics approach to CF genotype-independent, i.e., independent of the exact nature of the genetic mutation underlying the reduced CFTR expression or reduced CFTR function in CF.

Figure 12:
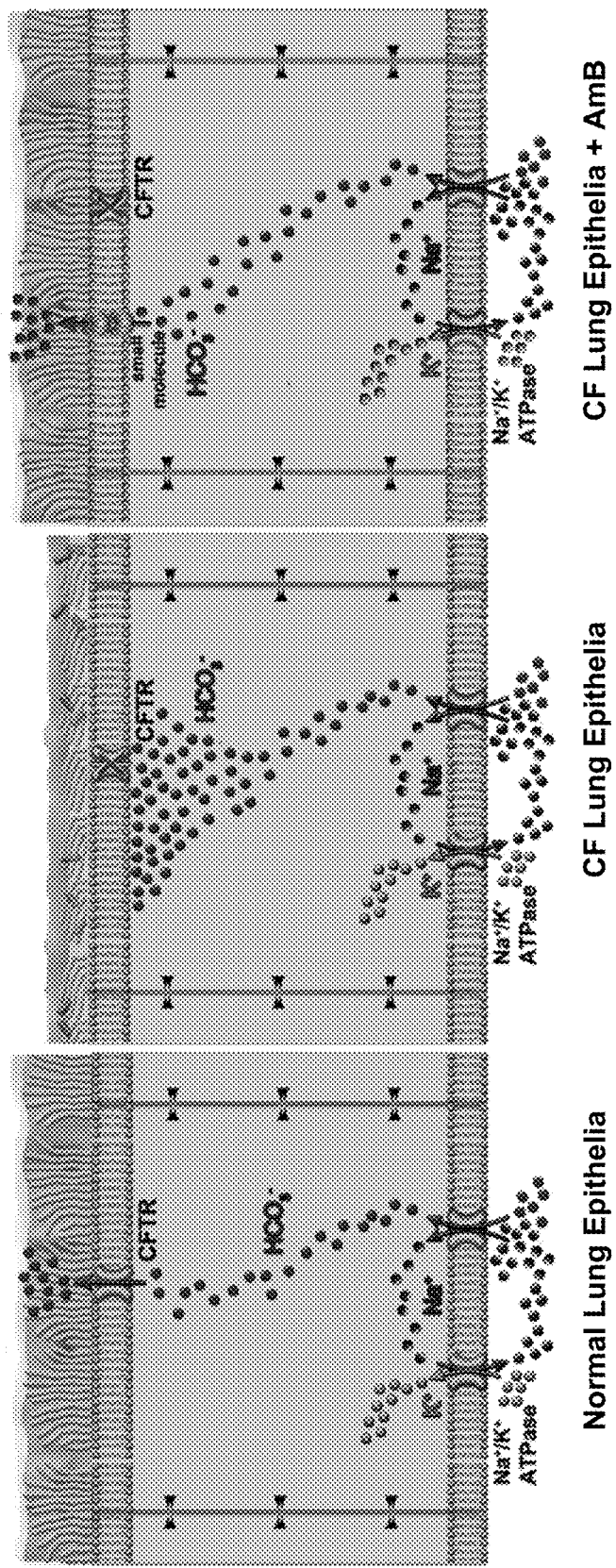
FIG. 12 depicts schematic representations of normal lung epithelia, cystic fibrosis lung epithelia, and cystic fibrosis lung epithelia plus AmB.

A thin layer of airway surface liquid (ASL) represents the sole barrier between the human lung and the environment. In normal ASL physiology, basolateral pumps and channels drive bicarbonate flux into polarized epithelial cells, and a primary function of CFTR is to passively release this bicarbonate through the apical membrane into the ASL (FIG. 12, left). A leading model of CF pathophysiology predicts that loss-of-function of CFTR reduces apical bicarbonate release, leading to acidification of the ASL and a build-up of bicarbonate ions inside the epithelial cells (FIG. 12, middle). This causes airway surface liquid (ASL) acidification, increases ASL viscosity, and decreases the activity of pH-sensitive antimicrobial proteins. These changes in the ASL impair the clearance and killing of bacteria, leaving patients vulnerable to the chronic airway infections that are the primary driver of morbidity and mortality. Alternative models suggest that CFTR also plays other important roles, such as modulating the activity of neighboring ion channels, and ruling out such alternative models experimentally has proven to be challenging. If the primary function of CFTR is to act as a passive conduit for bicarbonate, then a bicarbonate permeable small molecule-based channel in the apical membrane could harness the gradients that build up in CFTR-deficient epithelial cells to restore direction-selective bicarbonate secretion and thereby ASL physiology in a genotype agnostic manner (FIG. 12, right).

Figure 1:
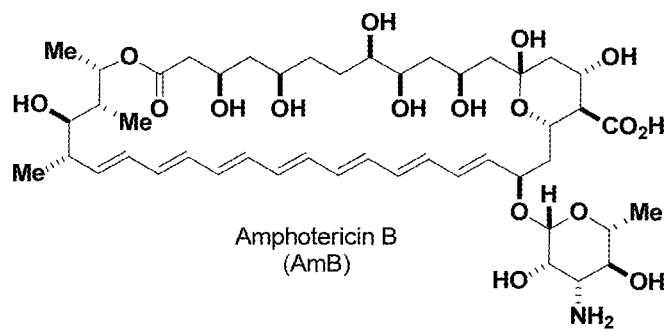
FIG. 1 depicts the structures of amphotericin B (AmB), C35-deoxy amphotericin B (C35deOAmB), and C3-deoxy amphotericin B (C3deOAmB).
Figure 1:
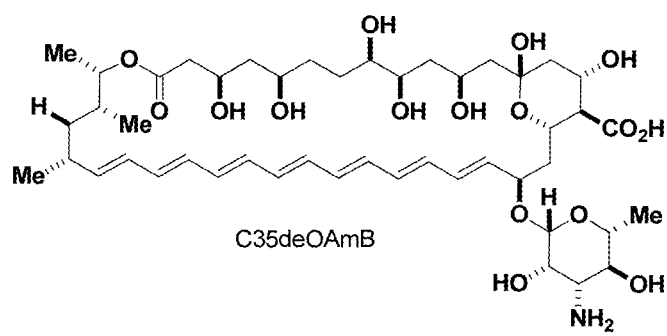
Figure 1:
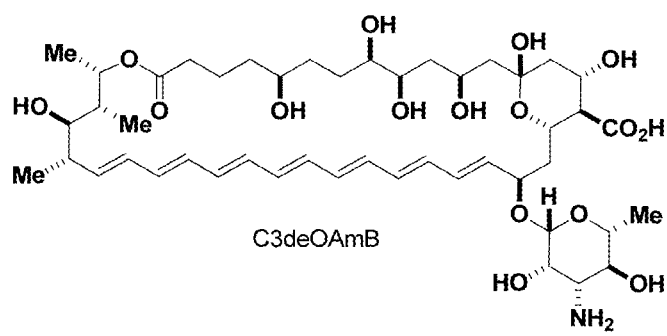
Figure 2:
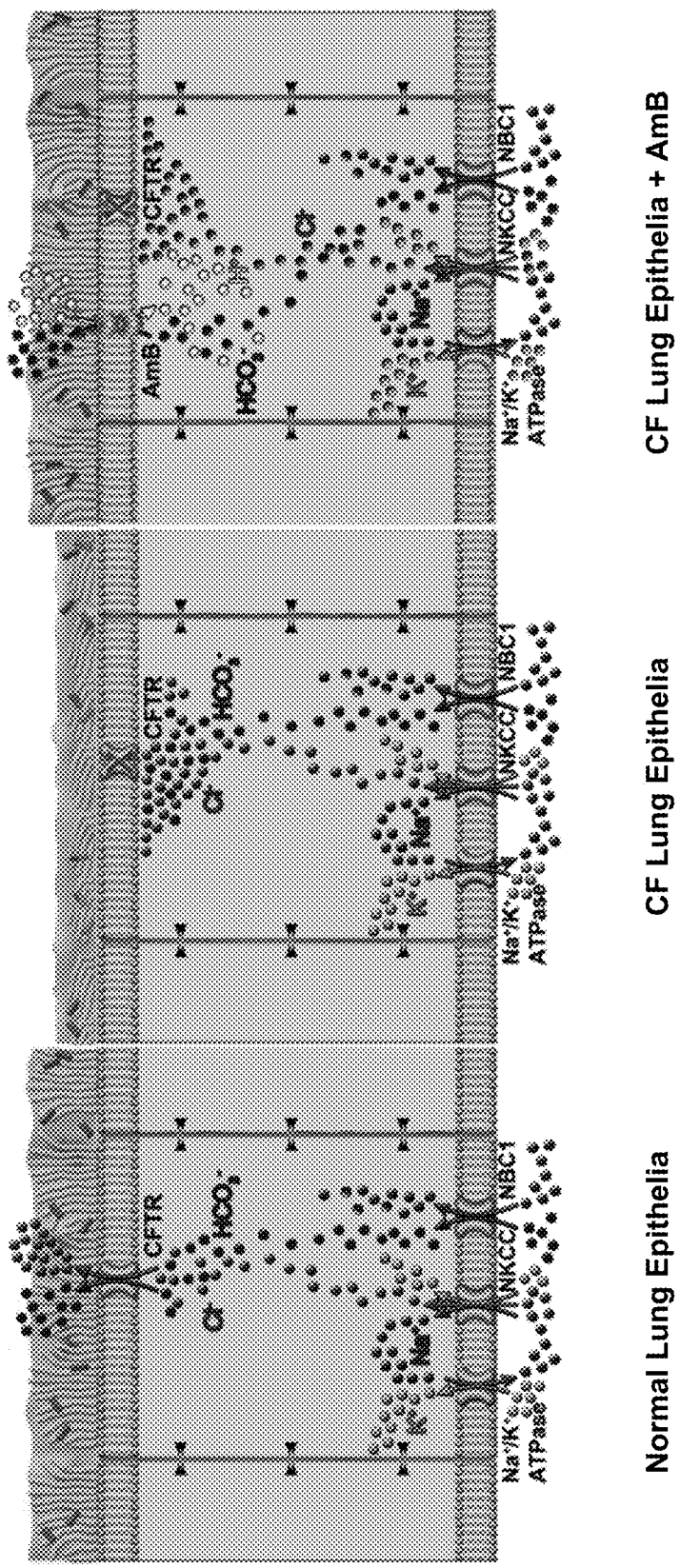
FIG. 2 depicts schematic representations of normal lung epithelia, cystic fibrosis lung epithelia, and cystic fibrosis lung epithelia plus AmB. Cystic fibrosis lung epithelia have reduced apical $Cl^-$ and $HCO_3^-$ secretion, altering mucus properties, as well as decreased airway surface liquid (ASL) pH, impairing antimicrobial activity.
Figure 13:
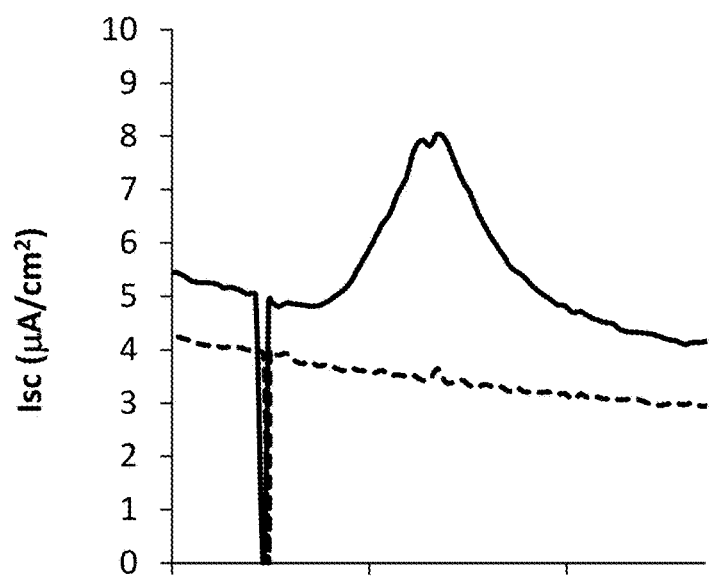
FIG. 13 depicts Ussing traces of 0.5 µM AmB (solid line) and of 0.5 µM C35deOAmB (dashed line).
Figure 14:
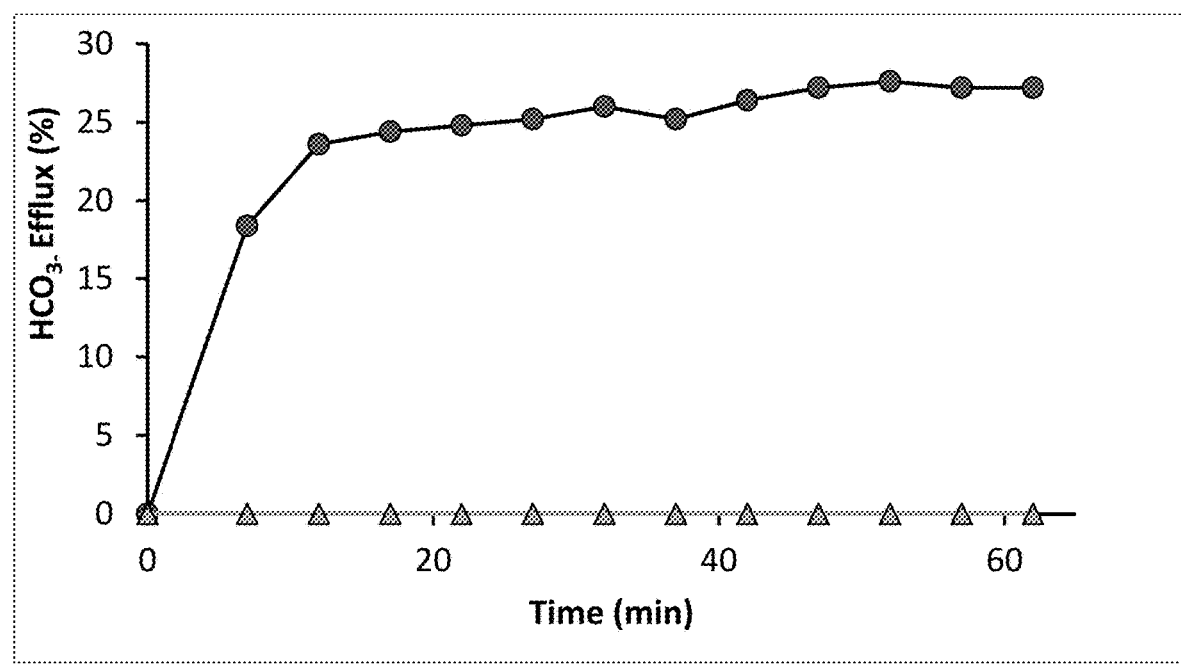
FIG. 14 depicts the effect of AmB on bicarbonate release from liposomes over time.

In some embodiments, a small molecule or a complex can permeabilize the apical membrane of differentiated human lung epithelia to bicarbonate. A series of natural and synthetic small molecules reported previously to permeabilize liposomes, cells, and/or nasal epithelia of mice to anions were tested for the capacity to increase short circuit current across CuFi-1 epithelial monolayers using an Ussing chamber. The clinically approved antifungal natural product amphotericin B (AmB) (FIG. 1) stood out as being exceptionally effective (FIG. 13). Little or no permeabilization of these same epithelia was observed with all of the other compounds tested, including a single-atom-deficient synthetic derivative of AmB, such as C35deOAmB (FIG. 12). The capacity for AmB to transport bicarbonate was tested using an adapted $^{13}C$ NMR-based assay in cholesterol-containing POPC liposomes. Robust and rapid release of $^{13}C$-labelled bicarbonate was observed from liposomes treated with AmB (FIG. 14).

In some embodiments, treatment with AmB, AmB and cholesterol, C3deOAmB and cholesterol, AmB and ergosterol, or C3deOAmB and ergosterol rescues one or more of ASL pH, viscosity, and antimicrobial activity in primary lung epithelia derived from CF.

It has been shown that protein ion channel-deficient yeast (trk1Δtrk2Δ) which lack functional Trk involved in passive transmembrane $K^+$ transport, can be restored to normal phenotype (growth) upon treatment with channel-forming AmB. Cioffi A G et al. (2015) *J Am Chem Soc* 137: 10096-10099.

AmB can permeabilize eukaryotic cells, such as yeast cells, to potassium and other ions. Ermishkin L N et al. (1977) *Biochim Biophys Acta* 470(3): 357-367. AmB is also highly toxic to yeast, and this toxicity was thought to be inextricably linked to its membrane permeabilization. However, we found that a synthesized derivative of AmB lacking a single oxygen atom at C35 (C35deOAmB) (FIG. 1) does not form ion channels, and yet still maintains potent fungicidal activity. Gray K C et al. (2012) *Proc Natl Acad Sci USA* 109(7): 2234-2239. Further studies revealed that AmB primarily kills yeast by binding and extracting sterols from membranes and is only cytotoxic when the amount of AmB exceeds that of ergosterol. Anderson T M et al. (2014) Nat Chem Biol 10(5): 400-406. Channel formation is not required. This enabled separation of the ion channel activity of AmB from its cell killing effects via administering at low doses and/or pre-complexation with sterols. AmB can restore growth in protein ion channel-deficient yeast. The range of doses for which growth rescue is observed can be extended by more than an order of magnitude when AmB is pre-complexed with the primary sterol in yeast, ergosterol. The non-channel-forming variant C35deOAmB failed to rescue yeast growth at any tested concentration In some embodiments, AmB is effective for increasing the pH of ASL in the lungs of CF patients, thereby improving airway antimicrobial activity and airway protection in these patients.

In some embodiments, pre-complexation of AmB with ergosterol substantially increases the therapeutic index for yeast growth rescue, i.e., preserves channel formation without potent fungicidal activity. Cioffi A G et al. (2015) *J Am Chem Soc* 137: 10096-10099.

Remarkably, AmB and cholesterol together, for example pre-formed complexes between AmB and cholesterol, are effective for increasing the pH of ASL in the lungs of CF patients, thereby improving airway antimicrobial activity and airway protection in these patients. In certain embodiments, the molar ratio of AmB:cholesterol is in the range from 1:2.6 to about 1:50. In certain embodiments, the molar ratio of AmB:cholesterol is in the range from about 1:3 to about 1:15.

Remarkably, C3deOAmB and cholesterol together, for example pre-formed complexes between C3deOAmB and cholesterol, are effective for increasing the pH of ASL in the lungs of CF patients, thereby improving airway antimicrobial activity and airway protection in these patients. In certain embodiments, the molar ratio of C3deOAmB:cholesterol is in the range from 1:2.6 to about 1:50. In certain embodiments, the molar ratio of C3deOAmB:cholesterol is in the range from about 1:3 to about 1:15.

AMBIOSOME® for Injection (Astellas Pharma US, Inc., Northbrook, IL) is a sterile, lyophilized preparation of AmB for intravenous infusion. Each vial contains 50 mg of amphotericin B intercalated into a liposomal membrane consisting of approximately 213 mg hydrogenated soy phosphatidylcholine; 52 mg cholesterol, 84 mg distearoylphosphatidyl-glycerol; 0.64 mg alpha tocopherol, together with 900 mg sucrose, and 27 mg disodium succinate hexahydrate as buffer. The molar ratio of AmB to cholesterol for this product is about 1:2.5.

Remarkably, AmB and ergosterol together, for example pre-formed complexes between AmB and ergosterol, are effective for increasing the pH of ASL in the lungs of CF patients, thereby improving airway antimicrobial activity and airway protection in these patients. In certain embodiments, the molar ratio of AmB:ergosterol is in the range from 1:2.6 to about 1:50. In certain embodiments, the molar ratio of AmB:ergosterol is in the range from about 1:3 to about 1:15.

Remarkably, C3deOAmB and ergosterol together, for example pre-formed complexes between C3deOAmB and ergosterol, are effective for increasing the pH of ASL in the lungs of CF patients, thereby improving airway antimicrobial activity and airway protection in these patients. In certain embodiments, the molar ratio of C3deOAmB:ergosterol is in the range from 1:2.6 to about 1:50. In certain embodiments, the molar ratio of C3deOAmB:ergosterol is in the range from about 1:3 to about 1:15.

Compositions of the Invention

In one aspect, provided herein is a composition comprising amphotericin B (AmB), a pharmaceutically acceptable salt or hydrate thereof; and a pharmaceutically acceptable carrier.

In certain embodiments, the composition is formulated for systemic administration.

In certain embodiments, the composition is formulated for intravenous administration.

In certain embodiments, the composition is formulated for pulmonary administration.

In certain embodiments, the composition is formulated for airway administration.

In certain embodiments, the composition is formulated for aerosol administration.

An aspect of the invention is a complex formed between (i) amphotericin B (AmB) a pharmaceutically acceptable salt or hydrate thereof, and (ii) cholesterol. This and similar complexes can be formed as disclosed herein, and they can be assayed by a method such as disclosed in the Examples. Anderson T M et al. (2014) *Nat Chem Biol* 10(5):404-406.

A "complex" as used herein refers to a conjugate formed between two or more component moieties, wherein the various component moieties are covalently linked. In certain embodiments, the complex may have a single or central component moiety to which all other component moieties are individually linked. In certain embodiments, each component moiety is linked to at least one other component moiety, i.e., without requiring a single or central component moiety to which all other component moieties are individually linked. For example, in certain embodiments, a complex may have a single or central AmB component moiety to which all cholesterol component moieties are individually linked.

In certain embodiments, the complex consists of (i) amphotericin B (AmB), or a pharmaceutically acceptable salt or hydrate thereof, and (ii) cholesterol.

In certain embodiments, the complex consists essentially of (i) amphotericin B (AmB), or a pharmaceutically acceptable salt or hydrate thereof, and (ii) cholesterol.

An aspect of the invention is a composition, comprising (i) amphotericin B (AmB), or a pharmaceutically acceptable salt or hydrate thereof, and (ii) cholesterol, wherein the molar ratio of AmB to cholesterol is greater than 1:2.4 (e.g., about 1:2, 1:1, 2:1, 3:1, 4:1, or 5:1) or in the range from 1:2.6 to about 1:50.

An aspect of the invention is a composition, comprising (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the composition consists of (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the composition consists essentially of (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the molar ratio of AmB to cholesterol is in the range from about 1:3 to about 1:15.

In certain embodiments, the molar ratio of AmB to cholesterol is in the range from about 1:4 to about 1:12.

In certain embodiments, the molar ratio of AmB to cholesterol is in the range from about 1:5 to about 1:10.

The AmB and the cholesterol are present in a molar ratio of AmB to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In certain embodiments, the AmB and the cholesterol are present as a complex. An example of how to prepare such a complex is disclosed in the Examples.

In certain embodiments, the composition is formulated for systemic administration.

In certain embodiments, the composition is formulated for intravenous administration.

In certain embodiments, the composition is formulated for pulmonary administration.

In certain embodiments, the composition is formulated for airway administration.

In certain embodiments, the composition is formulated for aerosol administration.

An aspect of the invention is a complex formed between (i) C3-deoxy amphotericin B (C3deOAmB), or a pharmaceutically acceptable salt or hydrate thereof, and (ii) cholesterol.

In certain embodiments, the complex consists of (i) C3deOAmB, or a pharmaceutically acceptable salt or hydrate thereof, and (ii) cholesterol.

In certain embodiments, the complex consists essentially of (i) C3deOAmB a pharmaceutically acceptable salt or hydrate thereof, and (ii) cholesterol.

An aspect of the invention is a composition, comprising (i) C3-deoxy amphotericin B (C3deOAmB), or a pharmaceutically acceptable salt or hydrate thereof, and (ii) cholesterol, wherein the molar ratio of C3deOAmB to cholesterol is in the range from 1:2.6 to about 1:50.

In certain embodiments, the composition consists of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the composition consists essentially of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the molar ratio of C3deOAmB to cholesterol is in the range from about 1:3 to about 1:15.

In certain embodiments, the molar ratio of C3deOAmB to cholesterol is in the range from about 1:4 to about 1:12.

In certain embodiments, the molar ratio of C3deOAmB to cholesterol is in the range from about 1:5 to about 1:10.

The C3deOAmB and the cholesterol are present in a molar ratio of C3deOAmB to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In certain embodiments, the C3deOAmB and the cholesterol are present as a complex.

In certain embodiments, the composition is formulated for systemic administration.

In certain embodiments, the composition is formulated for intravenous administration.

In certain embodiments, the composition is formulated for airway administration.

In certain embodiments, the composition is formulated for aerosol administration.

An aspect of the invention is a composition, comprising (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the composition consists of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the composition consists essentially of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the molar ratio of AmB to ergosterol is in the range from about 1:3 to about 1:15.

In certain embodiments, the molar ratio of AmB to ergosterol is in the range from about 1:4 to about 1:12.

In certain embodiments, the molar ratio of AmB to ergosterol is in the range from about 1:5 to about 1:10.

The AmB and the ergosterol are present in a molar ratio of AmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In certain embodiments, the AmB and the ergosterol are present as a complex.

In certain embodiments, the composition is formulated for systemic administration.

In certain embodiments, the composition is formulated for intravenous administration.

In certain embodiments, the composition is formulated for pulmonary administration.

In certain embodiments, the composition is formulated for airway administration.

In certain embodiments, the composition is formulated for aerosol administration.

An aspect of the invention is a complex, comprising (i) C3-deoxy amphotericin B (C3deOAmB), or a pharmaceutically acceptable salt or hydrate thereof, and (ii) ergosterol.

In certain embodiments, the complex consists of (i) C3-deoxy amphotericin B (C3deOAmB), or a pharmaceutically acceptable salt or hydrate thereof, and (ii) ergosterol.

In certain embodiments, the complex consists essentially of (i) C3-deoxy amphotericin B (C3deOAmB), or a pharmaceutically acceptable salt or hydrate thereof, and (ii) ergosterol.

An aspect of the invention is a composition, comprising (i) C3-deoxy amphotericin B (C3deOAmB), or a pharmaceutically acceptable salt or hydrate thereof, and (ii) ergosterol, wherein the molar ratio of C3deOAmB to ergosterol is in the range from 1:2.6 to about 1:50.

In certain embodiments, the composition consists of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the composition consists essentially of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the molar ratio of C3deOAmB to ergosterol is in the range from about 1:3 to about 1:15.

In certain embodiments, the molar ratio of C3deOAmB to ergosterol is in the range from about 1:4 to about 1:12.

In certain embodiments, the molar ratio of C3deOAmB to ergosterol is in the range from about 1:5 to about 1:10.

The C3deOAmB and the ergosterol are present in a molar ratio of C3deOAmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In certain embodiments, the C3deOAmB and the ergosterol are present as a complex.

In certain embodiments, the composition is formulated for systemic administration.

In certain embodiments, the composition is formulated for intravenous administration.

In certain embodiments, the composition is formulated for pulmonary administration.

In certain embodiments, the composition is formulated for airway administration.

In certain embodiments, the composition is formulated for aerosol administration.

Methods of the Invention

In one aspect, provided herein is a method of treating cystic fibrosis, comprising administering to a subject in need thereof a therapeutically effective amount of amphotericin B (AmB), or a pharmaceutically acceptable salt or hydrate thereof, thereby treating the cystic fibrosis.

An aspect of the invention is a method of treating cystic fibrosis, comprising administering to a subject in need thereof a therapeutically effective amount of a complex comprising (i) amphotericin B (AmB), or a pharmaceutically acceptable salt or hydrate thereof, and (ii) cholesterol, thereby treating the cystic fibrosis.

An aspect of the invention is a method of treating cystic fibrosis, comprising administering to a subject in need thereof a therapeutically effective amount of a composition comprising (i) amphotericin B (AmB), or a pharmaceutically acceptable salt or hydrate thereof, and (ii) cholesterol, thereby treating the cystic fibrosis.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In certain embodiments a subject is a human.

As used herein, the phrase "effective amount" refers to any amount that is sufficient to achieve a desired biological effect.

As used herein, the phrase "therapeutically effective amount" refers to any amount that is sufficient to achieve a desired therapeutic effect, e.g., treating cystic fibrosis.

In certain embodiments, the composition consists of (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the composition consists essentially of (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the AmB and the cholesterol are present in a molar ratio in the range from about 1:3 to about 1:15.

In certain embodiments, the AmB and the cholesterol are present in a molar ratio in the range from about 1:4 to about 1:12.

In certain embodiments, the AmB and the cholesterol are present in a molar ratio in the range from about 1:5 to about 1:10.

The AmB and the cholesterol are present in a molar ratio of Amb to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the AmB and the cholesterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of treating cystic fibrosis, comprising administering to a subject in need thereof a therapeutically effective amount of a complex comprising (i) C3-deoxy amphotericin B (C3deOAmB), or a pharmaceutically acceptable salt or hydrate thereof, and (ii) cholesterol, thereby treating the cystic fibrosis.

An aspect of the invention is a method of treating cystic fibrosis, comprising administering to a subject in need thereof a therapeutically effective amount of a composition comprising (i) C3-deoxy amphotericin B (C3deOAmB), or a pharmaceutically acceptable salt or hydrate thereof, and (ii) cholesterol, thereby treating the cystic fibrosis.

In certain embodiments, the composition consists of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the composition consists essentially of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the C3deOAmB and the cholesterol are present in a molar ratio in the range from about 1:3 to about 1:15.

In certain embodiments, the C3deOAmB and the cholesterol are present in a molar ratio in the range from about 1:4 to about 1:12.

In certain embodiments, the C3deOAmB and the cholesterol are present in a molar ratio in the range from about 1:5 to about 1:10.

The C3deOAmB and the cholesterol are present in a molar ratio of C3deOAmB to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the C3deOAmB and the cholesterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of treating cystic fibrosis, comprising administering to a subject in need thereof a therapeutically effective amount of a complex comprising (i) amphotericin B (AmB), or a pharmaceutically acceptable salt or hydrate thereof, and (ii) ergosterol, thereby treating the cystic fibrosis.

An aspect of the invention is a method of treating cystic fibrosis, comprising administering to a subject in need thereof a therapeutically effective amount of a composition comprising (i) amphotericin B (AmB), or a pharmaceutically acceptable salt or hydrate thereof, and (ii) ergosterol, thereby treating the cystic fibrosis.

In certain embodiments, the composition consists of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the composition consists essentially of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the AmB and the ergosterol are present in a molar ratio in the range from about 1:3 to about 1:15.

In certain embodiments, the AmB and the ergosterol are present in a molar ratio in the range from about 1:4 to about 1:12.

In certain embodiments, the AmB and the ergosterol are present in a molar ratio in the range from about 1:5 to about 1:10.

The AmB and the ergosterol are present in a molar ratio of AmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the AmB and the ergosterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of treating cystic fibrosis, comprising administering to a subject in need thereof a therapeutically effective amount of a complex comprising (i) C3-deoxy amphotericin B (C3deOAmB), or a pharmaceutically acceptable salt or hydrate thereof, and (ii) ergosterol, thereby treating the cystic fibrosis.

An aspect of the invention is a method of treating cystic fibrosis, comprising administering to a subject in need thereof a therapeutically effective amount of a composition comprising (i) C3-deoxy amphotericin B (C3deOAmB), or a pharmaceutically acceptable salt or hydrate thereof, and (ii) ergosterol, thereby treating the cystic fibrosis.

In certain embodiments, the composition consists of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the composition consists essentially of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the C3deOAmB and the ergosterol are present in a molar ratio in the range from about 1:3 to about 1:15.

In certain embodiments, the C3deOAmB and the ergosterol are present in a molar ratio in the range from about 1:4 to about 1:12.

In certain embodiments, the C3deOAmB and the ergosterol are present in a molar ratio in the range from about 1:5 to about 1:10.

The C3deOAmB and the ergosterol are present in a molar ratio of C3deOAmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the C3deOAmB and the ergosterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

In one aspect, provided herein is a method of increasing the pH of airway surface liquid in a subject having cystic fibrosis, comprising administering to a subject having cystic fibrosis a therapeutically effective amount of amphotericin B (AmB), or a pharmaceutically acceptable salt or hydrate thereof, thereby increasing the pH of airway surface liquid in the subject having cystic fibrosis.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of increasing the pH of airway surface liquid in a subject having cystic fibrosis, comprising administering to a subject having cystic fibrosis a therapeutically effective amount of a complex comprising (i) amphotericin B (AmB), or a pharmaceutically acceptable salt or hydrate thereof, and (ii) cholesterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) amphotericin B (AmB), or a pharmaceutically acceptable salt or hydrate thereof, and (ii) cholesterol, thereby increasing the pH of airway surface liquid in the subject having cystic fibrosis.

In certain embodiments, the composition consists of (i) amphotericin B (AmB), or a pharmaceutically acceptable salt or hydrate thereof, and (ii) cholesterol, wherein the molar ratio of AmB to cholesterol is in the range from 1:2.6 to about 1:50.

In certain embodiments, the composition consists essentially of (i) amphotericin B (AmB), or a pharmaceutically acceptable salt or hydrate thereof, and (ii) cholesterol, wherein the molar ratio of AmB to cholesterol is in the range from 1:2.6 to about 1:50.

The pH of airway surface liquid (ASL) in a subject can be measured using any technique known to those of skill in the art. For example, airway pH can be measured by placing a planar pH-sensitive probe on the tracheal surface. Pezzulo A A et al. (2012) *Nature* 487: 109-113.

The pH of ASL in a subject is said to be increased when it is measurably greater than the pH of ASL of an untreated subject. In one embodiment the pH of ASL in a subject is said to be increased when it is measurably greater than the pH of ASL of the same subject measured prior to or distant in time from treatment according to a method of the invention.

In certain embodiments, the increase in pH can be 0.01 pH unit to 2.0 pH unit. In certain embodiments, the increase in pH can be 0.01 pH unit to 1.0 pH unit. In certain embodiments, the increase in pH can be 0.01 pH unit to 0.5 pH unit. In certain embodiments, the increase in pH can be 0.01 pH unit to 0.4 pH unit. In certain embodiments, the increase in pH can be 0.01 pH unit to 0.3 pH unit. In certain embodiments, the increase in pH can be 0.01 pH unit to 0.2 pH unit. In certain embodiments, the increase in pH can be 0.01 pH unit to 0.1 pH unit.

In some embodiments, the increase in pH is by apical addition of any one of the compositions disclosed herein.

In some embodiments, the increase in pH of ASL correlates to alkalization of the apical solution. In some embodiments, the alkalization of the apical solution is bicarbonate-dependent.

In some embodiments, the increased apical chamber alkalization occurs in the presence of basolateral bicarbonate.

In some embodiments, the increase in ASL pH is not due to increasing CFTR activity/trafficking to the surface or disrupting membrane integrity.

In certain embodiments, the AmB and the cholesterol are present in a molar ratio in the range from about 1:3 to about 1:15.

In certain embodiments, the AmB and the cholesterol are present in a molar ratio in the range from about 1:4 to about 1:12.

In certain embodiments, the AmB and the cholesterol are present in a molar ratio in the range from about 1:5 to about 1:10.

The AmB and the cholesterol are present in a molar ratio of AmB to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the AmB and the cholesterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of increasing the pH of airway surface liquid in a subject having cystic fibrosis, comprising administering to a subject having cystic fibrosis a therapeutically effective amount of a complex comprising (i) C3-deoxy amphotericin B (C3deOAmB), or a pharmaceutically acceptable salt or hydrate thereof, and (ii) cholesterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) C3-deoxy amphotericin B (C3deOAmB), or a pharmaceutically acceptable salt or hydrate thereof, and (ii) cholesterol, thereby increasing the pH of airway surface liquid in the subject having cystic fibrosis.

In certain embodiments, the composition consists of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the composition consists essentially of (i) C3deOAmB, or a pharmaceutically acceptable salt or hydrate thereof, and (ii) cholesterol, wherein the molar ratio of C3deOAmB to cholesterol is in the range from 1:2.6 to about 1:50.

In certain embodiments, the C3deOAmB and the cholesterol are present in a molar ratio in the range from about 1:3 to about 1:15.

In certain embodiments, the C3deOAmB and the cholesterol are present in a molar ratio in the range from about 1:4 to about 1:12.

In certain embodiments, the C3deOAmB and the cholesterol are present in a molar ratio in the range from about 1:5 to about 1:10.

The C3deOAmB and the cholesterol are present in a molar ratio of C3deOAmB to cholesterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the C3deOAmB and the cholesterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of increasing the pH of airway surface liquid in a subject having cystic fibrosis, comprising administering to a subject having cystic fibrosis a therapeutically effective amount of a complex comprising (i) amphotericin B (AmB), or a pharmaceutically acceptable salt or hydrate thereof, and (ii) ergosterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) amphotericin B (AmB), or a pharmaceutically acceptable salt or hydrate thereof, and (ii) ergosterol, thereby increasing the pH of airway surface liquid in the subject having cystic fibrosis.

In certain embodiments, the composition consists of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the composition consists essentially of (i) amphotericin B (AmB), or a pharmaceutically acceptable salt or hydrate thereof, and (ii) ergosterol, wherein the molar ratio of AmB to ergosterol is in the range from 1:2.6 to about 1:50.

In certain embodiments, the AmB and the ergosterol are present in a molar ratio in the range from about 1:3 to about 1:15.

In certain embodiments, the AmB and the ergosterol are present in a molar ratio in the range from about 1:4 to about 1:12.

In certain embodiments, the AmB and the ergosterol are present in a molar ratio in the range from about 1:5 to about 1:10.

The AmB and the ergosterol are present in a molar ratio of AmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the AmB and the ergosterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

An aspect of the invention is a method of increasing the pH of airway surface liquid in a subject having cystic fibrosis, comprising administering to a subject having cystic fibrosis a therapeutically effective amount of a complex comprising (i) C3-deoxy amphotericin B (C3deOAmB), or a pharmaceutically acceptable salt or hydrate thereof, and (ii) ergosterol, thereby increasing the pH of airway surface liquid in the subject having cystic fibrosis.

An aspect of the invention is a method of increasing the pH of airway surface liquid in a subject having cystic fibrosis, comprising administering to a subject having cystic fibrosis a therapeutically effective amount of a composition comprising (i) C3-deoxy amphotericin B (C3deOAmB), or a pharmaceutically acceptable salt or hydrate thereof, and (ii) ergosterol, thereby increasing the pH of airway surface liquid in the subject having cystic fibrosis.

In certain embodiments, the composition consists of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the composition consists essentially of (i) C3deOAmB, or a pharmaceutically acceptable salt or hydrate thereof, and (ii) ergosterol, wherein the molar ratio of C3deOAmB to ergosterol is in the range from 1:2.6 to about 1:50.

In certain embodiments, the C3deOAmB and the ergosterol are present in a molar ratio in the range from about 1:3 to about 1:15.

In certain embodiments, the C3deOAmB and the ergosterol are present in a molar ratio in the range from about 1:4 to about 1:12.

In certain embodiments, the C3deOAmB and the ergosterol are present in a molar ratio in the range from about 1:5 to about 1:10.

The C3deOAmB and the ergosterol are present in a molar ratio of C3deOAmB to ergosterol. In certain embodiments, the molar ratio is about 1:3 to about 1:50. In certain embodiments, the molar ratio is about 1:4 to about 1:50. In certain embodiments, the molar ratio is about 1:5 to about 1:50. In certain embodiments, the molar ratio is about 1:6 to about 1:50. In certain embodiments, the molar ratio is about 1:7 to about 1:50. In certain embodiments, the molar ratio is about 1:8 to about 1:50. In certain embodiments, the molar ratio is about 1:9 to about 1:50. In certain embodiments, the molar ratio is about 1:10 to about 1:50. In certain embodiments, the molar ratio is about 1:11 to about 1:50. In certain embodiments, the molar ratio is about 1:12 to about 1:50. In certain embodiments, the molar ratio is about 1:13 to about 1:50. In certain embodiments, the molar ratio is about 1:14 to about 1:50. In certain embodiments, the molar ratio is about 1:15 to about 1:50. In certain embodiments, the molar ratio is about 1:16 to about 1:50. In certain embodiments, the molar ratio is about 1:17 to about 1:50. In certain embodiments, the molar ratio is about 1:18 to about 1:50. In certain embodiments, the molar ratio is about 1:19 to about 1:50. In certain embodiments, the molar ratio is about 1:20 to about 1:50. In certain embodiments, the molar ratio is about 1:21 to about 1:50. In certain embodiments, the molar ratio is about 1:22 to about 1:50. In certain embodiments, the molar ratio is about 1:23 to about 1:50. In certain embodiments, the molar ratio is about 1:24 to about 1:50. In certain embodiments, the molar ratio is about 1:25 to about 1:50. In certain embodiments, the molar ratio is about 1:26 to about 1:50. In certain embodiments, the molar ratio is about 1:27 to about 1:28. In certain embodiments, the molar ratio is about 1:29 to about 1:50. In certain embodiments, the molar ratio is about 1:30 to about 1:50. In certain embodiments, the molar ratio is about 1:31 to about 1:50. In certain embodiments, the molar ratio is about 1:32 to about 1:50. In certain embodiments, the molar ratio is about 1:33 to about 1:50. In certain embodiments, the molar ratio is about 1:34 to about 1:50. In certain embodiments, the molar ratio is about 1:35 to about 1:50. In certain embodiments, the molar ratio is about 1:36 to about 1:50. In certain embodiments, the molar ratio is about 1:37 to about 1:50. In certain embodiments, the molar ratio is about 1:38 to about 1:50. In certain embodiments, the molar ratio is about 1:39 to about 1:50. In certain embodiments, the molar ratio is about 1:40 to about 1:50.

In certain embodiments, the molar ratio is about 1:3 to about 1:40. In certain embodiments, the molar ratio is about 1:4 to about 1:40. In certain embodiments, the molar ratio is about 1:5 to about 1:40. In certain embodiments, the molar ratio is about 1:6 to about 1:40. In certain embodiments, the molar ratio is about 1:7 to about 1:40. In certain embodiments, the molar ratio is about 1:8 to about 1:40. In certain embodiments, the molar ratio is about 1:9 to about 1:40. In certain embodiments, the molar ratio is about 1:10 to about 1:40. In certain embodiments, the molar ratio is about 1:11 to about 1:40. In certain embodiments, the molar ratio is about 1:12 to about 1:40. In certain embodiments, the molar ratio is about 1:13 to about 1:40. In certain embodiments, the molar ratio is about 1:14 to about 1:40. In certain embodiments, the molar ratio is about 1:15 to about 1:40. In certain embodiments, the molar ratio is about 1:16 to about 1:40. In certain embodiments, the molar ratio is about 1:17 to about 1:40. In certain embodiments, the molar ratio is about 1:18 to about 1:40. In certain embodiments, the molar ratio is about 1:19 to about 1:40. In certain embodiments, the molar ratio is about 1:20 to about 1:40. In certain embodiments, the molar ratio is about 1:21 to about 1:40. In certain embodiments, the molar ratio is about 1:22 to about 1:40. In certain embodiments, the molar ratio is about 1:23 to about 1:40. In certain embodiments, the molar ratio is about 1:24 to about 1:40. In certain embodiments, the molar ratio is about 1:25 to about 1:40. In certain embodiments, the molar ratio is about 1:26 to about 1:40. In certain embodiments, the molar ratio is about 1:27 to about 1:28. In certain embodiments, the molar ratio is about 1:29 to about 1:40. In certain embodiments, the molar ratio is about 1:30 to about 1:40.

In certain embodiments, the molar ratio is about 1:3 to about 1:30. In certain embodiments, the molar ratio is about 1:4 to about 1:30. In certain embodiments, the molar ratio is about 1:5 to about 1:30. In certain embodiments, the molar ratio is about 1:6 to about 1:30. In certain embodiments, the molar ratio is about 1:7 to about 1:30. In certain embodiments, the molar ratio is about 1:8 to about 1:30. In certain embodiments, the molar ratio is about 1:9 to about 1:30. In certain embodiments, the molar ratio is about 1:10 to about 1:30. In certain embodiments, the molar ratio is about 1:11 to about 1:30. In certain embodiments, the molar ratio is about 1:12 to about 1:30. In certain embodiments, the molar ratio is about 1:13 to about 1:30. In certain embodiments, the molar ratio is about 1:14 to about 1:30. In certain embodiments, the molar ratio is about 1:15 to about 1:30. In certain embodiments, the molar ratio is about 1:16 to about 1:30. In certain embodiments, the molar ratio is about 1:17 to about 1:30. In certain embodiments, the molar ratio is about 1:18 to about 1:30. In certain embodiments, the molar ratio is about 1:19 to about 1:30. In certain embodiments, the molar ratio is about 1:20 to about 1:30.

In certain embodiments, the molar ratio is about 1:3 to about 1:20. In certain embodiments, the molar ratio is about 1:4 to about 1:20. In certain embodiments, the molar ratio is about 1:5 to about 1:20. In certain embodiments, the molar ratio is about 1:6 to about 1:20. In certain embodiments, the molar ratio is about 1:7 to about 1:20. In certain embodiments, the molar ratio is about 1:8 to about 1:20. In certain embodiments, the molar ratio is about 1:9 to about 1:20. In certain embodiments, the molar ratio is about 1:10 to about 1:20.

In certain embodiments, the molar ratio is about 1:3 to about 1:10. In certain embodiments, the molar ratio is about 1:4 to about 1:10. In certain embodiments, the molar ratio is about 1:5 to about 1:10.

In yet other embodiments, the molar ratio can be higher, as high as about 1:1 or even as high as 10:1.

In certain embodiments, the C3deOAmB and the ergosterol are present as a complex.

In certain embodiments, the composition is administered systemically.

In certain embodiments, the composition is administered intravenously.

In certain embodiments, the composition is administered to an airway of the subject. For example, the composition can be administered to an airway of the subject by bronchoalveolar lavage (BAL) or by aerosol. As used herein, an "airway of a subject" refers to any or all of the following pulmonary structures: trachea, bronchi, bronchioles, alveoli. In certain embodiments, an airway of a subject refers to a so-called conducting airway, i.e., any or all of the following pulmonary structures: trachea, bronchi, and bronchioles.

In certain embodiments, the composition is administered as an aerosol to an airway of the subject.

In another aspect, provided herein is a method of increasing the bicarbonate in airway surface liquid in a subject having cystic fibrosis, comprising administering to a subject having cystic fibrosis a therapeutically effective amount of amphotericin B (AmB), or a pharmaceutically acceptable salt or hydrate thereof, thereby increasing the bicarbonate of airway surface liquid in the subject having cystic fibrosis.

In certain embodiments, the composition is administered systemically.

In certain embodiments, the composition is administered intravenously.

In certain embodiments, the composition is administered to an airway of the subject.

In certain embodiments, the composition is administered as an aerosol to an airway of the subject.

In accordance with each of the foregoing embodiments, in certain embodiments, the subject is a human.

In accordance with each of the foregoing embodiments, in certain embodiments, the subject is less than 12 years old.

In accordance with each of the foregoing embodiments, in certain embodiments, the subject is at least 12 years old. For example, in certain embodiments, the subject is at least 12 to about 16 years old. In certain other embodiments, the subject is about 16 to about 24 years old. In certain other embodiments, the subject is about 24 to about 30 years old. In certain other embodiments, the subject is about 30 to about 40 years old. In certain other embodiments, the subject is about 40 to about 50 years old. In certain other embodiments, the subject is about 50 to about 60 years old. In certain other embodiments, the subject is about 60 to about 70 years old. In certain other embodiments, the subject is about 70 to about 80 years old.

In some embodiments, any of the methods disclosed herein permeabilize the apical membrane. In some embodiments, any of the methods disclosed herein permeabilize the apical membrane to protons. In some embodiments, any of the methods disclosed herein permeabilize the apical membrane to bicarbonate anions.

Over 1900 different CFTR mutations are found in CF patients, hundreds of which are confirmed to be disease causing through at least five different mechanisms of functional loss. There have been important recent advances in the development of genotype-specific small molecule drugs that bind to certain mutant forms of CFTR and thereby increase its activity. However, nearly half of all CF patients have CFTR genotypes that do not respond to current small molecule treatments. These include major truncations that yield a complete lack of functional CFTR protein and very rare mutations for which the mechanistic underpinnings of functional deficiency are unknown.

In some embodiments, any of the methods disclosed herein treat a mutation class of cystic fibrosis selected from the group consisting of I, II, III, IV, V, VI, U, and a combination thereof. In some embodiments, the mutation class is selected from the group consisting of I/I, II/U, and U/III.

In some embodiments, any of the methods disclosed herein treat a specific genotype of cystic fibrosis. In some embodiments, the genotype is selected from the group consisting of ΔF508/ΔF508, R553X/E60X, ΔF508/1717-1G→A, ΔF508/c.2052dupA, D293G/V520F, and G551D.

In some embodiments, any of the methods disclosed herein are genotype-independent treatments.

As used herein, the phrases "genotype-independent" or "genotype-agnostic" refer to any treatment that is independent of the exact nature of the genetic mutation underlying the reduced CFTR expression or reduced CFTR function in CF.

In some embodiments, any of the methods disclosed herein treat refractory or resistant cystic fibrosis. In some embodiments, the cystic fibrosis is refractory or resistant to one or more cystic fibrosis treatments (e.g., ivacaftor).

Formulations

The formulations of the invention may be administered in pharmaceutically acceptable solutions, which may routinely contain pharmaceutically acceptable concentrations of salt, buffering agents, preservatives, compatible carriers, adjuvants, and optionally other therapeutic ingredients.

Amphotericin B is commercially available in a number of formulations, including deoxycholate-based formulations and lipid-based (including liposomal) formulations. For purposes of this invention, AmB will typically be formulated with cholesterol. In certain embodiments, such formulation comprises a complex formed between AmB and cholesterol. In certain other embodiments, AmB will typically be formulated with ergosterol. In certain embodiments, such formulation comprises a complex formed between AmB and ergosterol.

For use in therapy, an effective amount of the active compound or composition of the invention can be administered to a subject by any mode that delivers the compound or composition to the desired location or surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

In certain preferred embodiments, the compound or composition is administered systemically. In certain preferred embodiments, the compound or composition is administered intravenously.

In certain preferred embodiments, the compound or composition is administered to an airway. In certain preferred embodiments, the compound or composition is administered as an aerosol to an airway.

Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, AmBerlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds and compositions for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569 (1990); Adjei et al., *Int J Pharmaceutics* 63:135-144 (1990) (leuprolide acetate); Braquet et al., *J Cardiovasc Pharmacol* 13 (suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colorado, March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569 (incorporated by reference), issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 μm, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, *Science* 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Dosing

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily doses measured in terms of AmB (or C3deOAmB) will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a composition of the invention may typically be from 0.1 mg/kg/day to 20 mg/kg/day as measured in terms of AmB (or C3deOAmB). Intravenous dosing thus may be similar to, or advantageously, may exceed maximal tolerated doses of AmB.

For any compound or composition described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Example 1. AmB Increases ASL pH in CF Human Lung Epithelia

We have previously proposed the usage of amphotericin B (AmB) as a potential therapeutic for cystic fibrosis, and have shown its ability to permeabilize human lung epithelia and increase ASL height. We next tested if AmB treatment could increase ASL pH in cultures of human CF lung epithelia with varied disease genotypes, using a fluorescent pH indicator.

Airway surface liquid (ASL) pH assay. ASL pH was studied using an established fluorescent dye assay using the Dextran, SNARF®-1, 70,000 MW ratiometric dye (Thermo Fisher D3304). Mature, differentiated CuFi-1 (ATCC CRL-4013) epithelial monolayers were grown on Corning Costar 0.4 μm Transwell Clear Polyester Membrane cell culture inserts (Corning 3470). CuFi epithelia were treated with perfluorinated hydrocarbon (PFC) vehicle, AmB, AmB:Chol or Chol and incubated for the time course of the experiment at 37° C. On the day of imaging, 100 μL of a suspension of SNARF-dextran in PFC was added to the apical side of the monolayers. Monolayers were imaged 2 hours after dye addition. The monolayers were placed on 100 μL of Ultroser G media on a 10 mm glass bottom Fluorodish for imaging (World Precision Instruments). Five images per membrane were taken on a Zeiss LSM 880 confocal microscope at 40× water immersion. These images were analyzed using ImageJ to determine the green to red ratio of each image. Solutions of known pH were used to calibrate pH detection using this system.

Figure 3A:
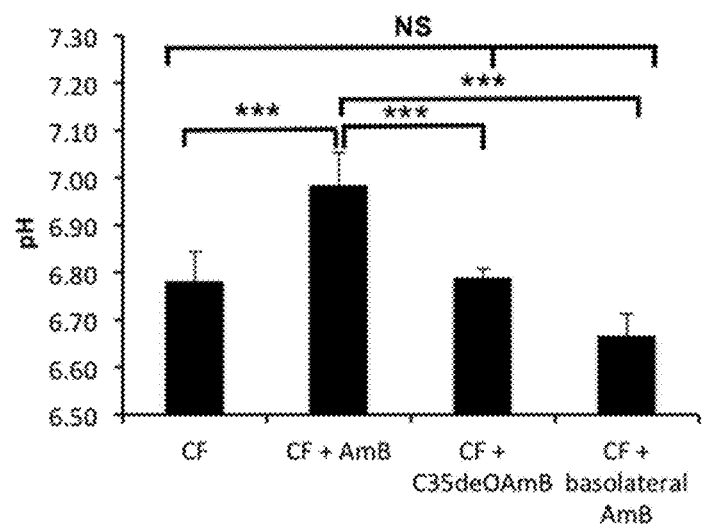
FIG. 3A is a bar graph depicting the ability of apical, but not basolateral, AmB to increase ASL pH in cystic fibrosis (CF) primary human lung epithelia. The figure also shows the lack of effect of apical C35deOAmB. ***, $p<0.001$; NS, not statistically significant.

Results. AmB increased ASL pH in human CF lung epithelia by about 0.2 pH units after 48 hours of apical incubation (FIG. 3A). This result was completely independent of patient donor genotype.

Example 2. C35deOAmB does not Increase ASL pH in Human CF Lung Epithelia

The observed sustained increase in transepithelial conductance by the AmB channel is the first line of evidence that AmB is forming ion channels in human lung epithelia. To further test this hypothesis, a single-atom-modified variant of AmB, C35deOAmB, which we previously have shown to be unable to permeabilize lipid membranes, was utilized. Because it cannot form ion channels, C35deOAmB is an important probe for determining if the observed effect of AmB on human lung epithelia is specifically mediated by its ion channel activity.

Figure 3B:
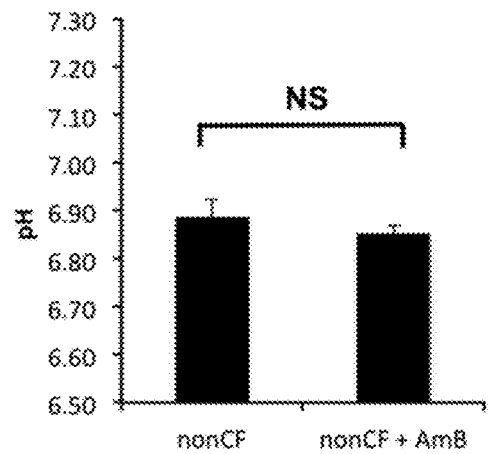
FIG. 3B is a bar graph depicting the absence of effect of apical AmB on ASL pH of control (non-CF) primary human lung epithelia. NS, not statistically significant.

Results. In contrast to AmB, C35deOAmB at any tested concentration was unable to increase ASL pH as compared to an untreated control (FIG. 3A). Demonstrating that AmB-mediated permeabilization of the apical membrane specifically causes this restoration, no increase in ASL pH was observed upon adding AmB to the basolateral surface (FIG. 3A). Moreover, AmB treatment had no effect of the pH of non-CF epithelia (FIG. 3B), supporting the hypothesis that an ion imbalance caused by the absence of CFTR is necessary for the AmB channel to have an impact on transepithelial ion transport.

Example 3. AmB-Mediated Increase in ASL pH is not Due to Disrupting Membranes or Increasing CFTR Activity Non-CF (control) and CF primary human lung epithelia were prepared and maintained in vitro as previously described. Pezzulo A A et al. (2012) *Nature* 487: 109-113. For example, epithelial cells were isolated from the trachea and bronchi by enzymatic digestion, seeded onto collagen-coated semi-permeable membranes (0.6 cm$^2$ Millicell-PCF; Millipore, Bedford, MA), and grown at the air-liquid interface as previously described in Karp P H et al. (2002) In Wise C., *Epithelial Cell Culture Protocols*, Humana Press, Inc. 188: 115-137. Culture medium, a 1:1 mixture of Dulbecco's modified Eagle's medium and Ham's F12 medium (DMEM/F12), was supplemented with 2% Ultroser G (PALL France SAS; Saint Germain-en-Laye, France). Differentiated epithelia were used at least 14 days after seeding.

Figure 4:
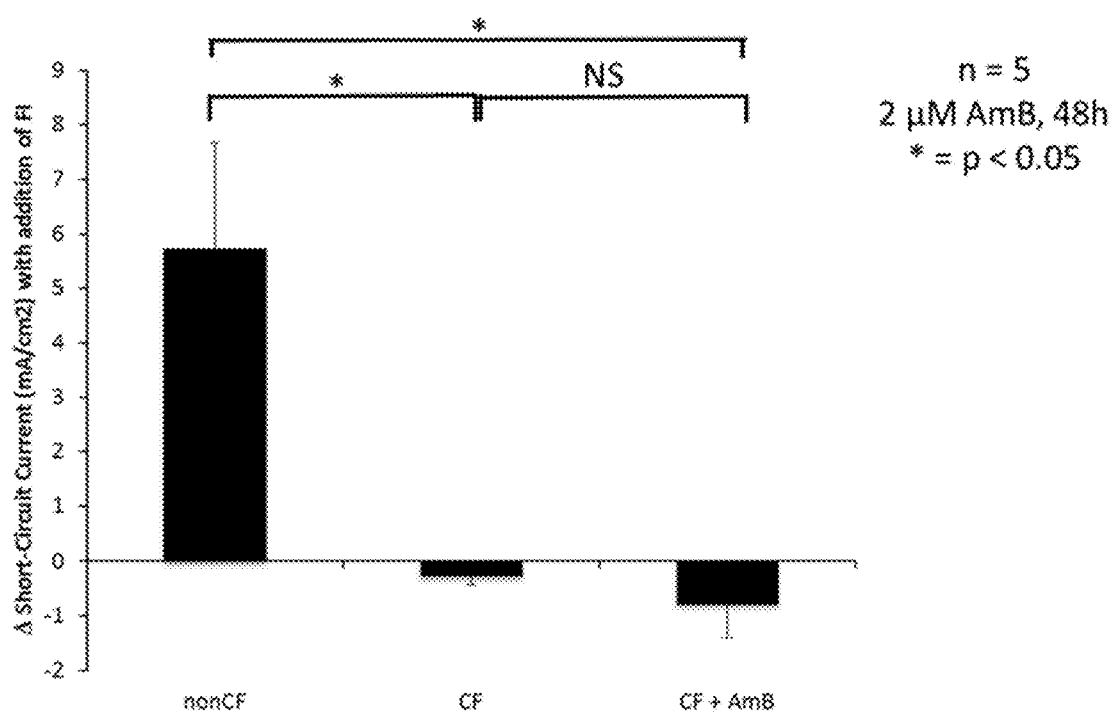
FIG. 4 is a bar graph depicting that AmB-mediated increase in ASL pH is not due to disrupting of membranes or increasing CFTR activity.

These cells were treated with AmB at a final concentration of 2 μM for 48 h, and then change in short-circuit current was measured. Representative results are shown in FIG. 4.

As shown in the figure, untreated non-CF primary human lung epithelia had significantly increased change in short-circuit current compared to untreated CF primary human lung epithelia. Also as shown in the figure, AmB-treated CF primary human lung epithelia had no significant difference in change of short-circuit current compared to untreated CF primary human lung epithelia. These results indicate that AmB-mediated increase in ASL pH is not due to disrupting membranes or increasing CFTR activity.

Example 4. AmB Increases ASL pH in a Time-Dependent Manner

Figure 5A:
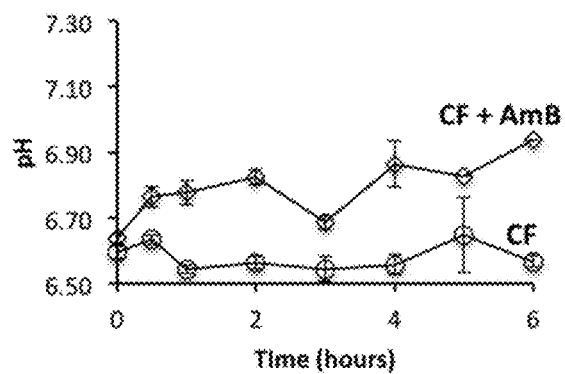
FIG. 5A is a graph depicting the effect of AmB on ASL pH over time.
Figure 5B:
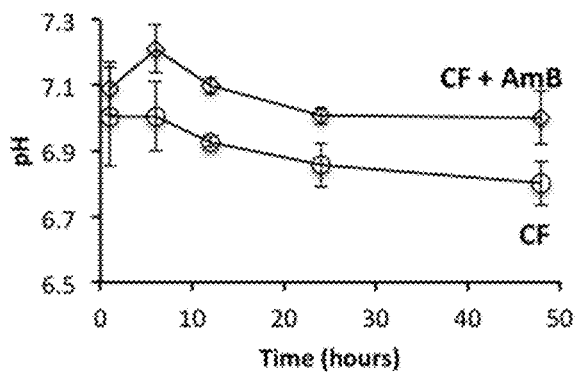
FIG. 5B is a graph depicting the effect of AmB on ASL pH over time.

The timecourse of the AmB effect was tested both in the short-term after acute addition (up to 6 hours) and in the long-term (up to 48 hours). It was found that AmB increases ASL pH in a time-dependent manner, with sustained effect for at least 48 h (FIG. 5A, FIG. 5B).

Example 5. AmB Decreases ASL Viscosity in CF Primary Human Lung Epithelia

Figure 6:
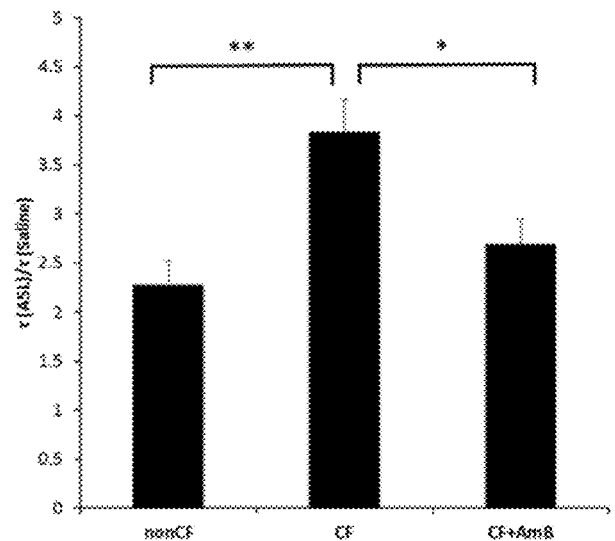
FIG. 6 is a bar graph depicting that AmB decreases ASL viscosity (t) in CF primary human epithelia independent of patient genotype.

Non-CF (control) and CF primary human lung epithelia were prepared and maintained in vitro as previously described. Pezzulo A A et al. (2012) Nature 487: 109-113. These cells were treated with AmB at a final concentration of 2 μM for 48 h, and then ASL viscosity was measured. Representative results are shown in FIG. 6.

As shown in the figure, untreated CF primary human lung epithelia had significantly increased ASL viscosity compared to untreated non-CF primary human lung epithelia. Also as shown in the figure, AmB-treated CF primary human lung epithelia had significantly decreased ASL viscosity compared to untreated CF primary human lung epithelia, and nearly the same as for untreated non-CF primary human lung epithelia. These results were independent of patient sample genotype.

Figure 7:
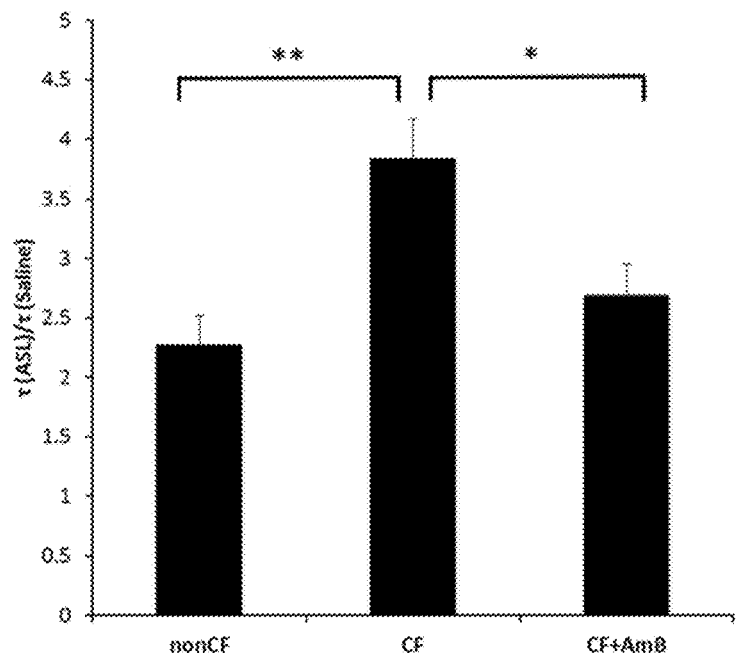
FIG. 7 is a bar graph depicting that AmB increases ASL bacterial killing in CF primary human epithelia independent of patient genotype.

Example 6. AmB Increases ASL Bacterial Killing in CF Primary Human Lung Epithelia CF primary human lung epithelia were prepared and maintained in vitro as previously described. Pezzulo A A et al. (2012) Nature 487: 109-113. These cells were treated with AmB or C35deOAmB at a final concentration of 2 μM for 1 minute, then washed and maintained in culture for 48 h, and then bacterial killing was measured. Representative results are shown in FIG. 7.

As shown in the figure, percent killing increased from about 25 percent to about 40 percent with the exposure to AmB ($p<0.0001$). Also as shown in the figure, percent killing was not significantly changed from control with the exposure to C35deOAmB. These results were independent of patient sample genotype.

Example 7. AmB Increases ASL pH in a Concentration-Dependent Manner

Figure 8:
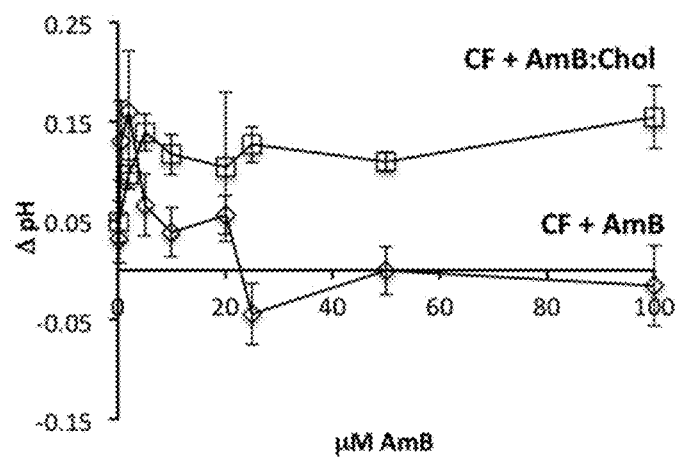
FIG. 8 is a graph depicting dose dependence of change in ASL pH in cystic fibrosis lung epithelia with pre-formed AmB-cholesterol complexes or AmB alone.

A range of AmB doses was tested, up to the limit of solubility, 100 μM suspension in PFC It was found that AmB increases ASL pH in a dose-dependent manner. The pH increased with dose up to 2 μM suspension in PFC. However, this effect started to decrease thereafter and dropped to about 0.05 pH units below the starting pH by 25 μM and beyond (FIG. 8). This rapid drop-off in efficacy at higher concentrations represents a potential limitation for clinical application of this strategy, as it can be very challenging to tightly control the concentrations of drug in the targeted tissue.

Example 8. Pre Formed Complexes of AmB:Cholesterol Extend the Window of Concentrations Over which AmB Restores ASL pH We next asked whether pre-complexation of AmB with cholesterol could mitigate some type of AmB-mediated cholesterol extraction/sequestration that may be driving the reduction in pH restoration at higher AmB concentrations. Specifically, we tested the activity of a pre-formed AmB:cholesterol complex.

Preparation of an amphotericin B:cholesterol complex. To make a pre-complexed aggregate of AmB and cholesterol (Chol) for the studies herein, Chol was first prepared as a 4 mg/mL in $CHCl_3$ stock solution. 965 μL of this solution was added to a 7 mL glass vial and the solvent removed under a gentle stream of nitrogen gas. 1 mL of a DMSO solution of 2 mM AmB was then added to the solid Chol to make a 10 mM final Chol concentration, a 1:5 mole ratio Chol:AmB suspension. A small stir bar was added to this suspension, and the vial was capped and heated to 80° C. for one hour in an aluminum heating block to allow Chol to fully dissolve, stirring at 300 rpm. The resulting AmB:Chol solution was then allowed to cool to room temperature. This solution was left to complex at room temperature for another 30 minutes before dividing into 100 μg aliquots and lyophilized overnight. AmB alone was also prepared in DMSO solution and lyophilized in 100 μg aliquots for these studies.

Figure 9:
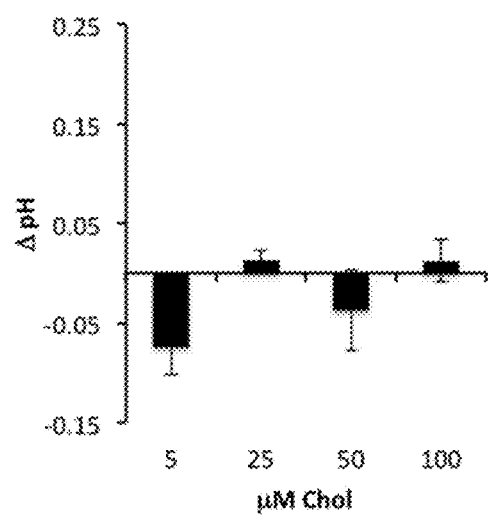
FIG. 9 is a bar graph depicting lack of effect of cholesterol alone on ASL pH.

Results. Pre-formed complex of AmB:cholesterol in a stoichiometric 1:5 ratio retained permeabilization in the Ussing chamber. Strikingly, this complex was able to extend the window of concentrations over which AmB restores ASL pH out to the limit of solubility, 100 μM (FIG. 8). Cholesterol alone was unable to increase ASL pH (FIG. 9). Thus, an AmB:cholesterol complex is superior to AmB alone as a functional surrogate for the missing CFTR protein in cystic fibrosis lung epithelia.

Figure 10A:
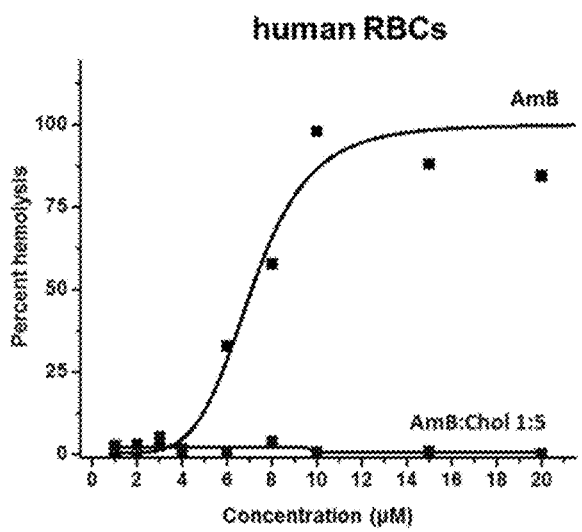
FIG. 10A is a graph depicting that pre-complexation of AmB with cholesterol protects human red blood cells (RBCs) against toxicity.

Example 9. Pre-Complexation of AmB with Cholesterol Protects Human Red Blood Cells Against Toxicity but Preserves Permeabilization of CF Human Lung Epithelia Human red blood cells (RBCs) were separated from whole blood by centrifugation and then exposed to AmB or pre-formed AmB:Chol complexes (1:5) (Example 8) over a range of concentrations up to 20 μM. Hemolysis was then measured. Representative results are shown in FIG. 10A. As shown in the figure, while uncomplexed AmB had 50 percent hemolysis at about 7 μM and 100 percent hemolysis at about 10 μM, pre-formed AmB:Chol complexes had essentially no hemolysis even at 20 μM.

Figure 10B:
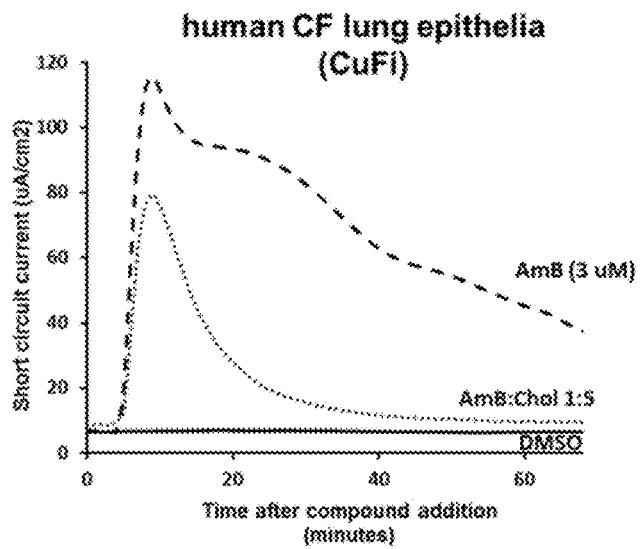
FIG. 10B is a graph depicting that pre-complexation of AmB with cholesterol preserves permeabilization of human CF lung epithelia.

In a separate set of experiments, CuFi-1 cells in culture were treated with AmB in DMSO, pre-formed AmB:Chol complexes (1:5), or DMSO alone, and then short-circuit current was measured over time out to about 70 minutes. Results are shown in FIG. 10B. As shown in the figure, pre-formed AmB:Chol complexes induced a short-term, lower increase in short-circuit current compared to uncomplexed AmB.

Example 10. Synthesis of C3deOAmB

AmB derivative C3deOAmB was generated in an efficient 9-step synthesis as shown in Scheme 1. Starting with the natural product, a series of functional group protections delivered intermediate 1 (Scheme 1). Gratifyingly, exposure of 1 to NaHMDS at low temperatures chemoselectively eliminated the C3 p-methoxyphenyl acetal, presumably via an E1cB type mechanism, yielding intermediate enone 2. Subsequent site-selective Stryker reduction of carbonyl-conjugated C3,C4 double bond providing deoxygenated intermediate 3. A final series of deprotections provided the targeted single-atom modified variant, C3deOAmB.

mixing time of 400 μs. These conditions revealed cross peaks for internuclear $^{13}C$-$^{13}C$ distances of ~4-6 Å. In order to properly identify new intermolecular AmB-Erg cross peaks the ($^{1}H$)—$^{13}C$—($^{1}H$-$^{1}H$)—$^{13}C$ spectra were acquired back-to-back under identical conditions, including and signal averaging, adjusting the total measurement time based on the amount of material. The rotors of POPC:U-$^{13}C$-AmB:Erg (10:1:1 molar ratio) and POPC:U-$^{13}C$-AmB:$^{13}C$-Erg (10:1:1 molar ratio) were packed with ~25 mg and the

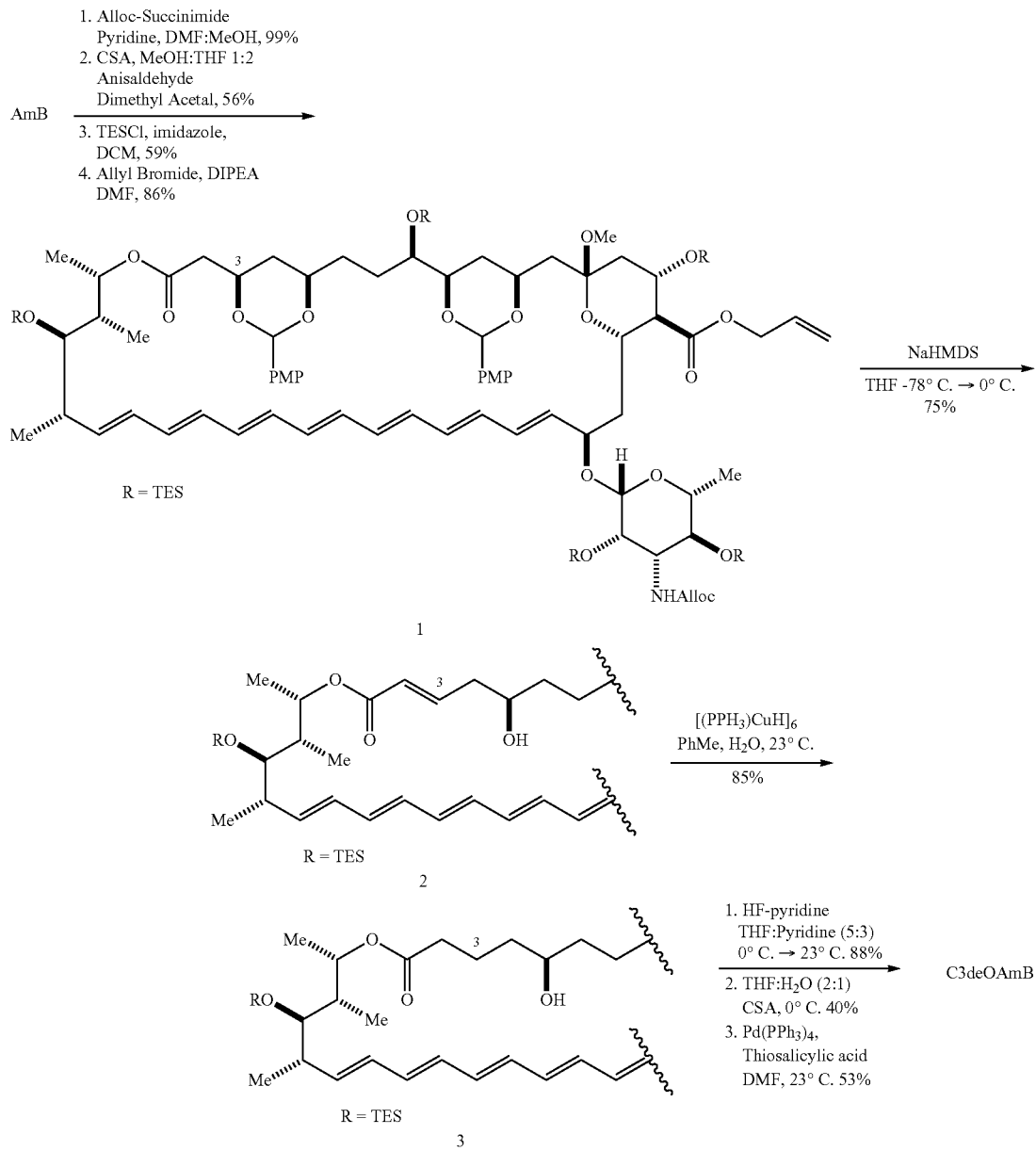

Scheme 1: Synthesis of C3deOAmB

Figure 11:
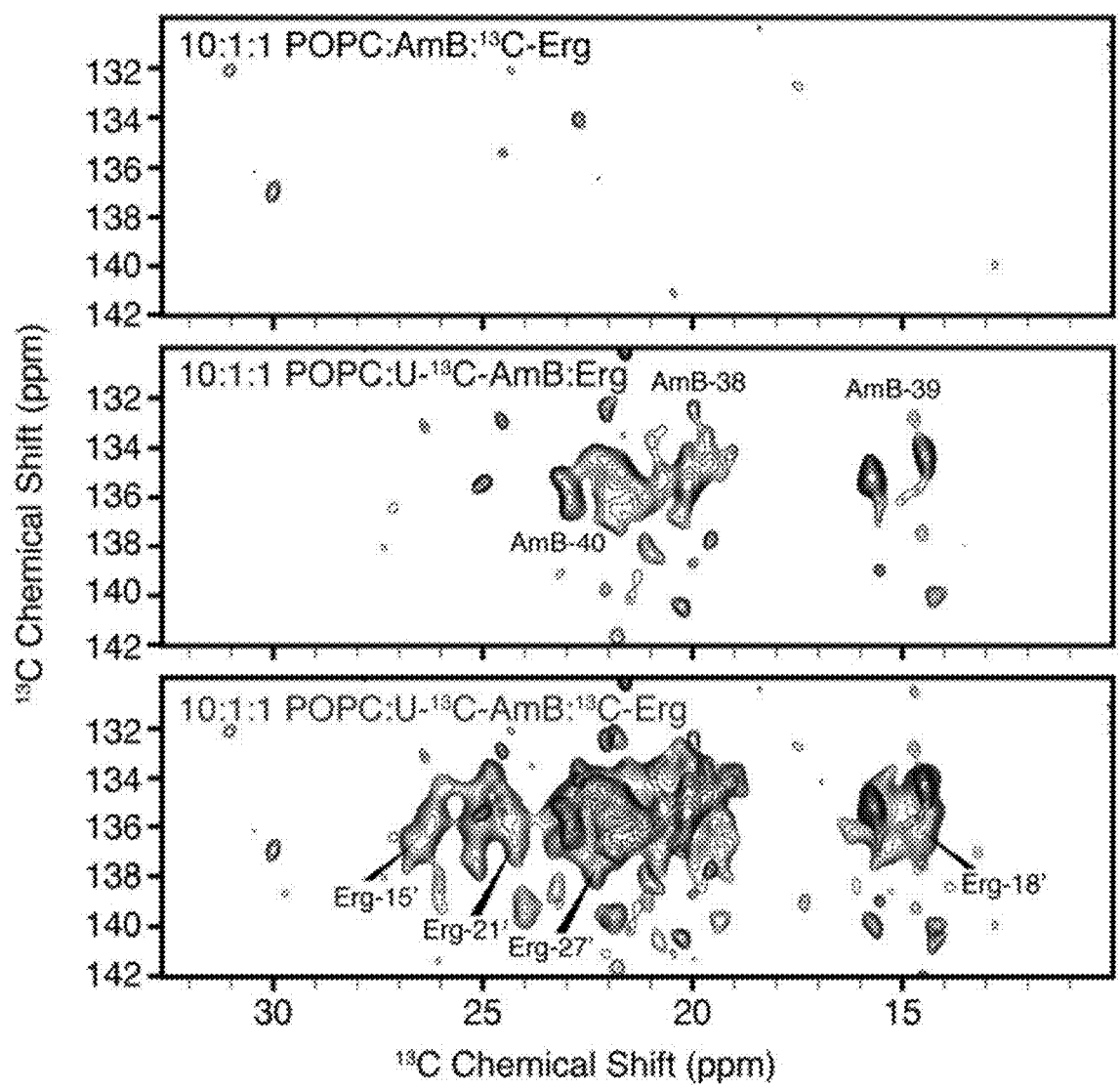
FIG. 11 is a group of three graphs depicting NMR spectra of $^{13}C$ labeled amphotericin B-ergosterol (AmB-Erg) complexes.

Example 11. NMR Analysis of AmB-Erg Complexes ($^{1}H$)—$^{13}C$—($^{1}H$-$^{1}H$)—$^{13}C$ SSNMR experiments were performed at 10° C., at an MAS rate 11.628 kHz, with the heteronuclear contact time ($t_{HC}$) set to 400 μs, and $^{1}H$-$^{1}H$ spectra signal averaged for 7.8 days each. The 10:1:1 POPC:AmB:$^{13}C$-Erg sample was ~16 mg and therefore signal averaged for 13.6 days. The three spectra were all processed identically, with 40 and 75 Hz $^{13}C$ line broadening applied in the direct and indirect dimensions, respectively. Results are shown in FIG. 11.

Figure 15A:
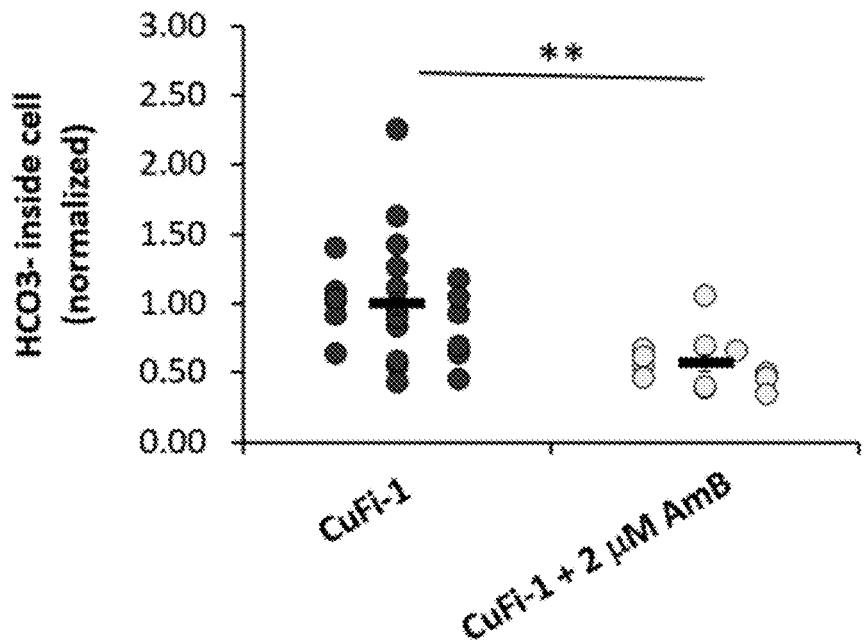
FIG. 15A is a graph depicting the effect of AmB on intracellular bicarbonate in cystic fibrosis CuFi-1 human lung epithelia. **, $p<0.01$.
Figure 15B:
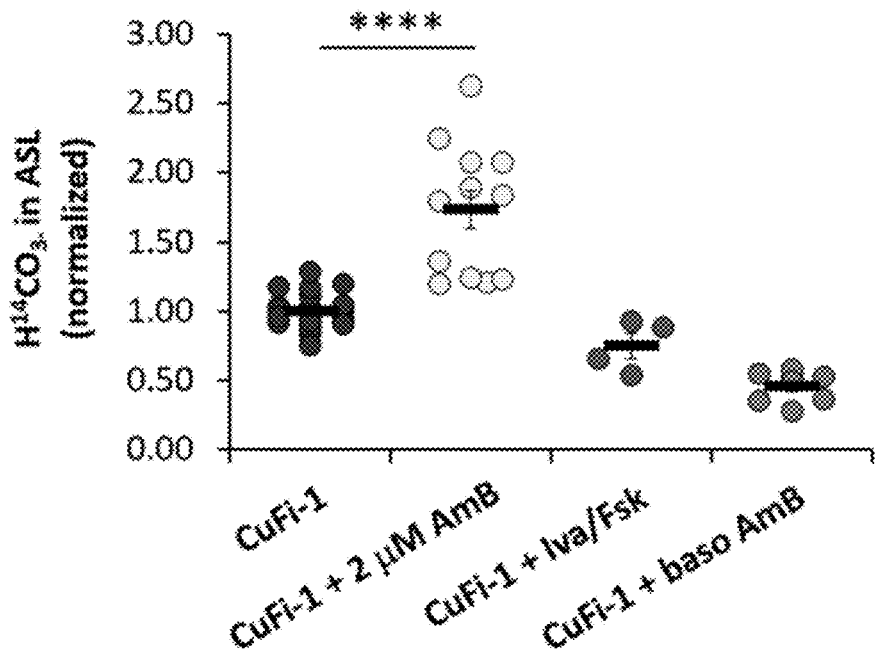
FIG. 15B is a graph depicting the ability of apical, but not basolateral, AmB to increase bicarbonate in ASL in cystic fibrosis CuFi-1 cells. The figure also shows the lack of effect of ivacaftor in CuFi-1 cells. ****, $p<0.0001$.
Figure 15C:
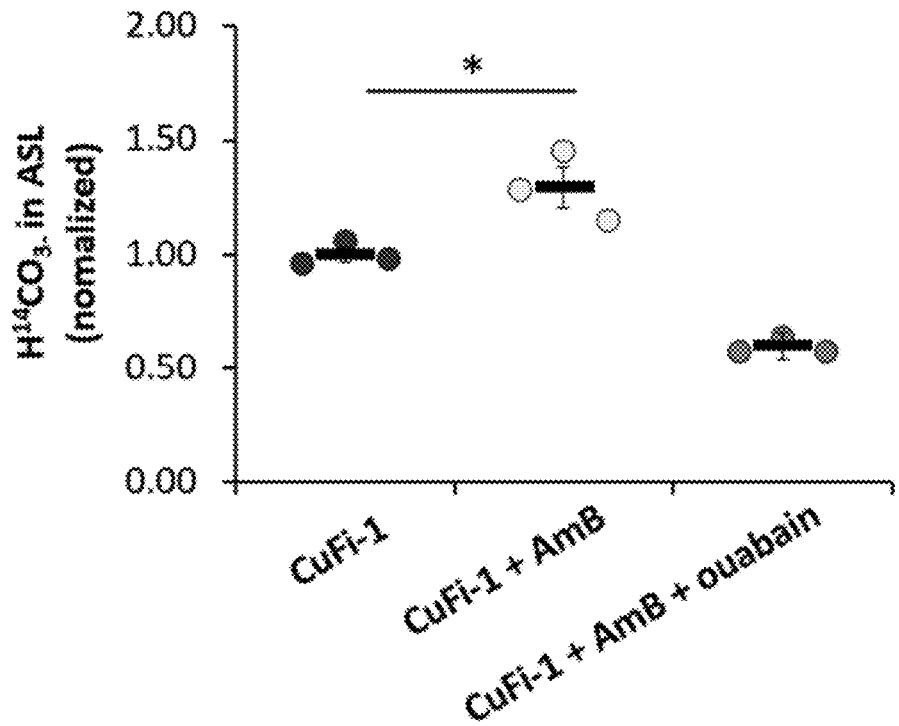
FIG. 15C is a graph depicting the ability of AmB to increase bicarbonate in ASL in CuFi-1 cells, but not in combination with ouabain, which blocks bicarbonate import. *, $p<0.05$.

Example 12. AmB Increases ASL Bicarbonate in CF Primary Human Lung Epithelia $^{14}$C bicarbonate was administered to the basolateral side of monolayers to trace ion movement through the cells over time. Epithelial monolayers grown from the patient-derived lung epithelial cell line CuFi-1 (ΔF508/ΔF508) were also studied. The genotype ΔF508/ΔF508 represents about 46.5% of all CF patients and is considered a relatively severe deficiency. Permeabilization of the apical membrane to bicarbonate anions with AmB could correct the flux abnormality resulting from the loss of CFTR. Upon treatment with 2 µM AmB for 48 hours, a decrease in intracellular $^{14}$C bicarbonate and an increase in ASL $^{14}$C bicarbonate compared to CuFi-1 alone was observed (FIGS. 15A and 15B). Basolateral treatment of AmB was also unable to increase apical transport of bicarbonate, demonstrating that the membrane-permeabilizing activity of AmB is specific to the side of addition (FIG. 15B). Inhibition of the basolateral Na$^+$/K$^+$ ATPase with ouabain abrogated the AmB-mediated increase in bicarbonate transport to the ASL, consistent with the blocking of bicarbonate import (FIG. 15C).

Ivacaftor, a small molecule potentiator that increases the open probability of CFTR channels with a specific type of gating defect, represents a major advance for the small subset of CF patients (2-4%) with a G551D allele or others in this less severe class of mutations. Remarkably, albeit only partially restoring CFTR activity, this drug has demonstrated substantial increases in lung function and overall quality of life in this select patient population. B. W. Ramsey et al. (2011) *New England Journal of Medicine* 365, 1663-1672. Some patients with similar gating mutations have also seen benefit, but other gating mutations, such as V520F, do not appear to respond. F. Van Goor, et al., (2014) *J. Cystic Fibrosis* 13, 29-36. Using ASL pH changes and its downstream effects as markers for CF rescue in primary sinonasal epithelial cell culture from a patient with a G551D gating mutation, it was found that ivacaftor increased ASL pH by about 0.2 pH units and decreased viscosity by about two units relative to control. E. H. Chang et al., *Int Forum Allergy Rhinol* 5, 178-181 (2015). Changes to antimicrobial activity could not be tested due to the inherent bactericidal properties of the drug. This drug also substantially improved lung function in CF patients having a G551D mutation, as evidenced by a 10% increase in predicted FEV$_1$ and an over 20% increase in event-free subjects in patients with this mutation over 48 weeks of treatment. This new understanding of the pathophysiology of CF and quantifiable in vitro changes in ASL physiology caused by ivacaftor can thus serve as benchmarks for the evaluation of alternative approaches for addressing the loss-of-function of CFTR. It is important to note that while ivacaftor is able to restore the whole function of the CFTR protein, AmB would be mimicking only a single function of CFTR in bicarbonate transport, and this distinction may also enable us to probe which role of CFTR could have the most immediate impact on physiology.

Figure 16:
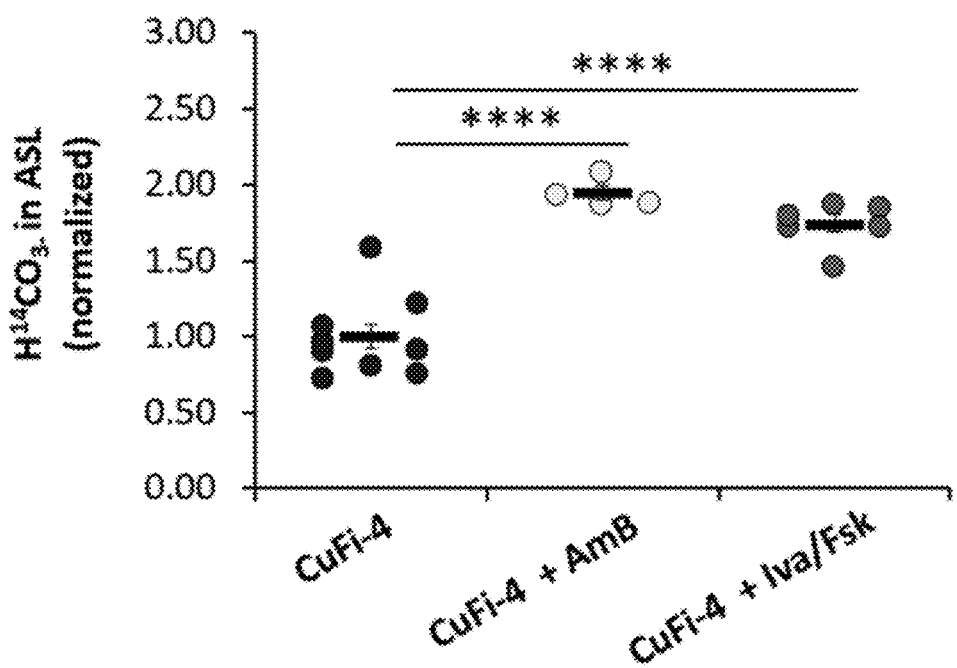
FIG. 16 is a graph depicting the ability of AmB and ivacaftor to increase bicarbonate in ASL in cystic fibrosis CuFi-4 cells. ****, $p<0.0001$.

Ivacaftor is a clinically approved and effective drug to treat cystic fibrosis, and it was used as a control in some of the experiments. Following literature precedent for in vitro ivacaftor administration, CuFi-4 (ΔF508/G551D) epithelia were treated with forskolin (Fsk) to promote phosphorylation of CFTR and ivacaftor (Iva) to potentiate conductance through the channel. E. H. Chang et al., *Int Forum Allergy Rhinol* 5, 178-181 (2015); F. Van Goor et al. (2009) *Proc. Natl. Acad. Sci.* 106, 18825-18830. As is expected for this genotype-specific small molecule, ivacaftor was able to increase the ASL $^{14}$C bicarbonate in CuFi-4 monolayers but not in CuFi-1 monolayers (FIGS. 15B and 16). In contrast, AmB was able to significantly increase ASL $^{14}$C bicarbonate in both cell lines (FIGS. 15B and 16). This provides evidence that while both ivacaftor and AmB increase bicarbonate transport, AmB is operating through a genotype-agnostic mechanism.

Figure 17:
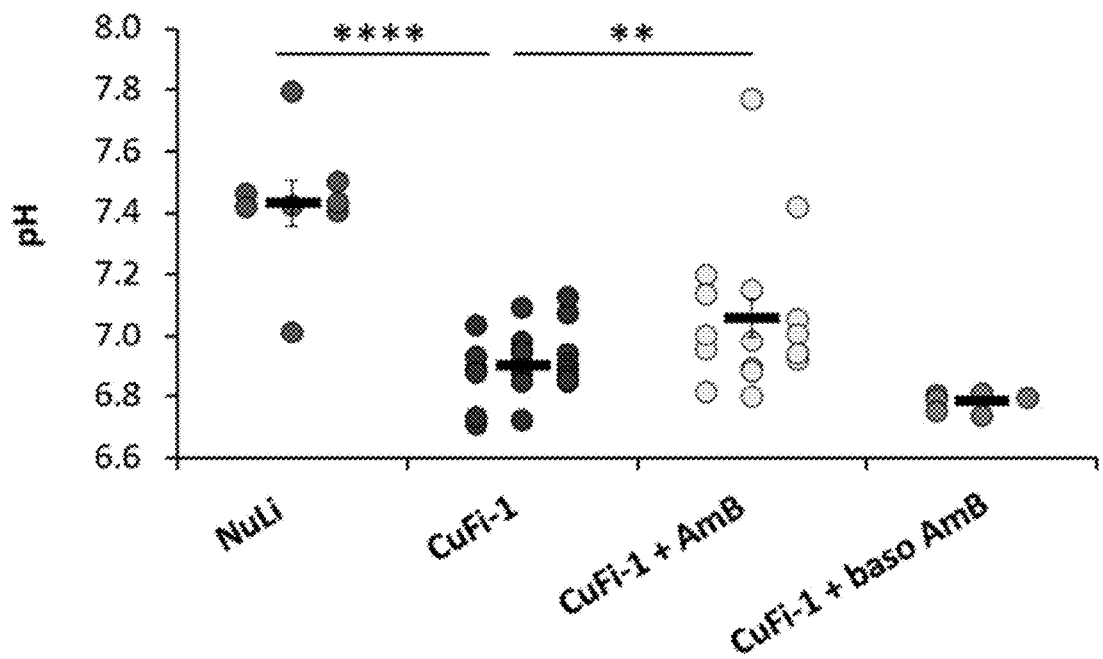
FIG. 17 is a graph depicting the ability of apical, but not basolateral, AmB to increase ASL pH in cystic fibrosis CuFi-1 cells. The figure also shows that CuFi-1 cells have reduced pH compared to NuLi cells. , $p<0.01$; **, $p<0.0001$.

Example 13. AmB Increases ASL pH in CF Human Lung Epithelia in a Bicarbonate-Dependent Manner Using a ratiometric fluorescent pH dye, CuFi-1 has reduced pH in comparison to NuLi epithelial monolayers (FIG. 17). Pezzulo A A et al. (2012) *Nature* 487: 109-113; Shah V S et al. (2016) *Science* 351: 503-507. AmB was found to increase ASL pH in CuFi-1 (FIG. 17). Basolateral addition of AmB was unable to increase ASL pH, consistent with the $^{14}$C bicarbonate studies (FIG. 17).

Figure 18:
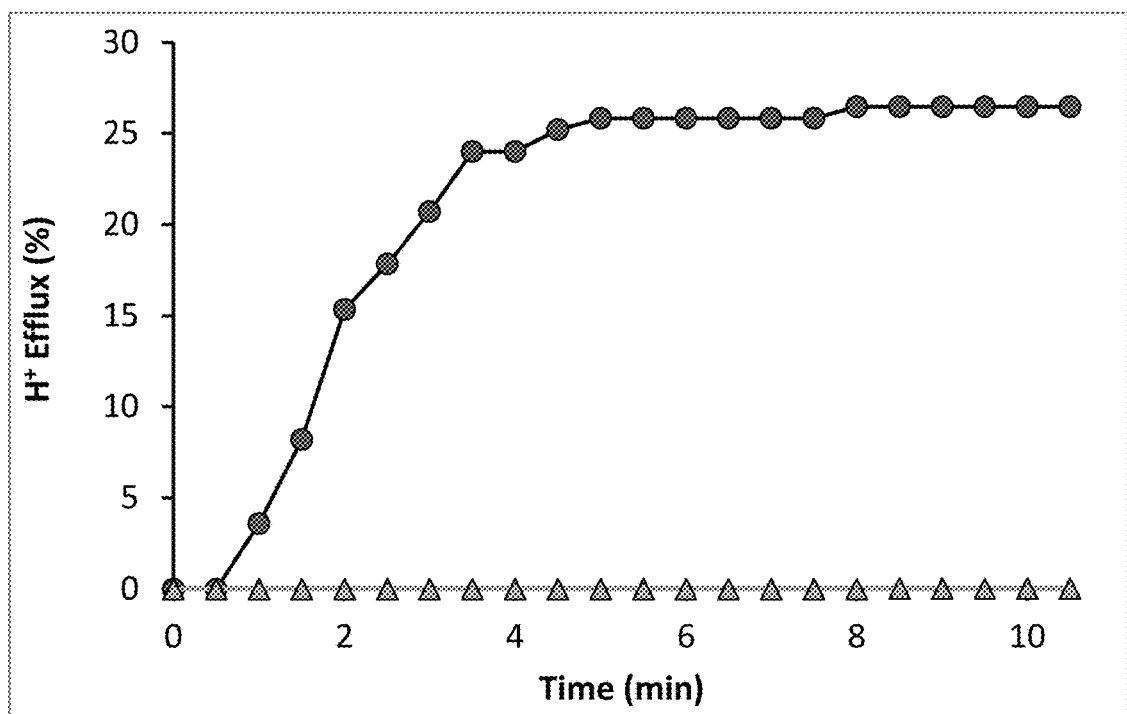
FIG. 18 depicts the effect of 1:100 AmB:lipid (circles) compared to DMSO (triangles) on proton release.
Figure 19:
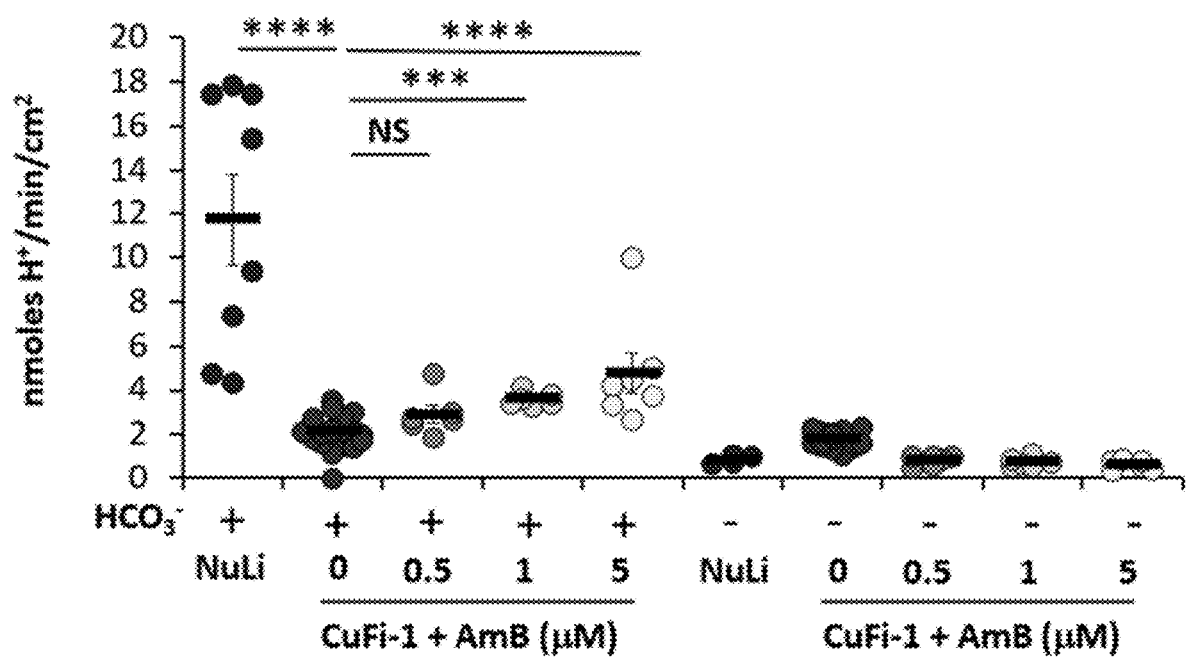
FIG. 19 is a graph depicting the ability of AmB to increase apical chamber alkalization of cystic fibrosis CuFi-1 cells in the presence of basolateral bicarbonate. The figure also shows that CuFi-1 cells have reduced apical chamber alkalization compared to NuLi cells in the presence of basolateral bicarbonate. No change in apical chamber alkalization was observed in bicarbonate-free buffer. *, p<0.001; **, p<0.0001; NS, not statistically significant.

AmB is also able to transport protons, so this presented an alternative mechanism by which the small molecule could influence ASL pH (FIG. 18). To directly probe whether AmB-mediated bicarbonate transport causes the ASL pH increase, pH-stat experiments were performed in large NuLi and CuFi-1 epithelial monolayers either in the presence of bicarbonate or in bicarbonate-free solution. Cho, D Y, et al., (2009) *Am J Rhinol Allergy* 23, e10-13; Cho, D Y, et al., (2011) *Int Forum Allergy Rhinol* 1, 123-127. Addition of AmB increased apical chamber alkalization of CuFi-1 epithelial monolayers in a dose-dependent fashion in the presence of basolateral bicarbonate (FIG. 19). To address the potential role of proton absorption in the alkalization of the ASL, these experiments were repeated in bicarbonate-free buffer. AmB did not increase apical chamber alkalization in the absence of bicarbonate, providing evidence that AmB-mediated alkalization of the apical solution is bicarbonate-dependent (FIG. 19).

Figure 20A:
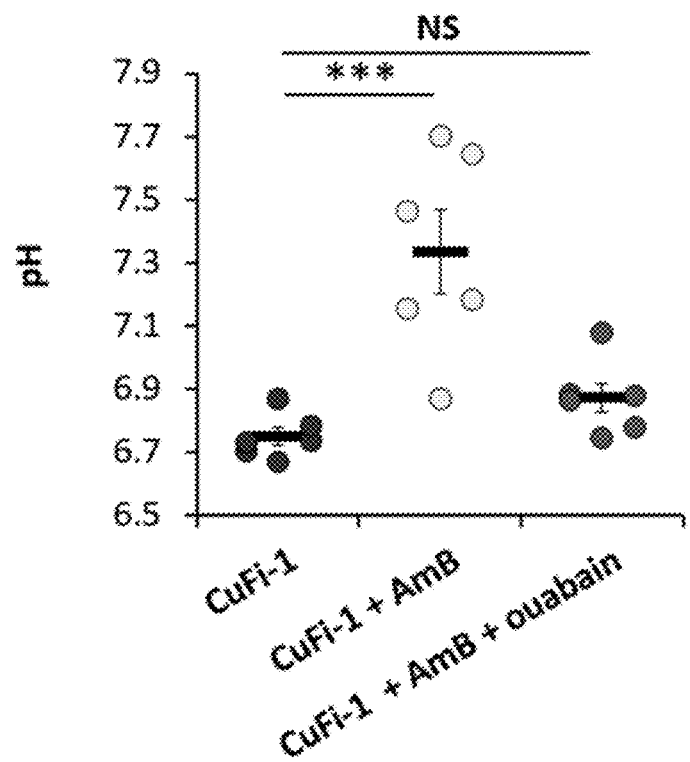
FIG. 20A is a graph depicting the ability of AmB to increase ASL pH in CuFi-1 cells, but not in combination with ouabain, which blocks bicarbonate import. ***, p<0.001; NS, not statistically significant.
Figure 20B:
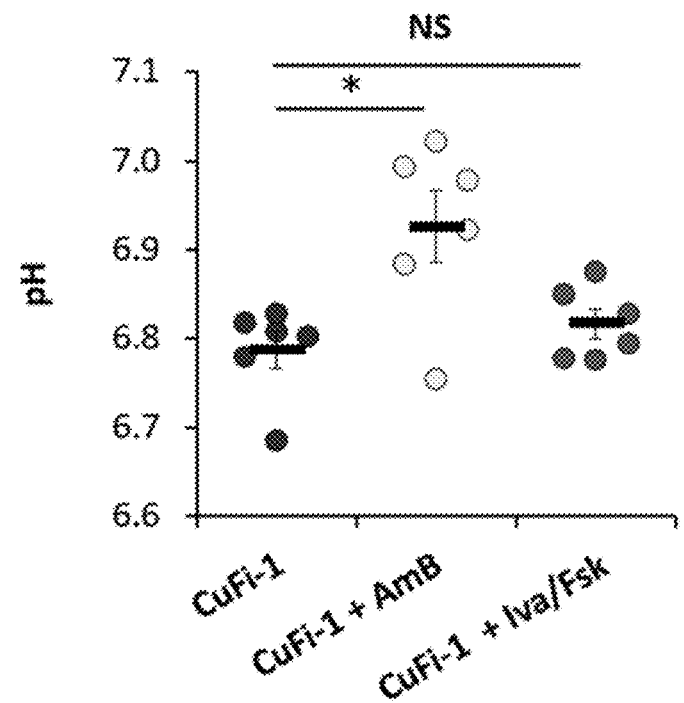
FIG. 20B is a graph depicting the ability of AmB to increase ASL pH in cystic fibrosis CuFi-1 cells. The figure also shows the lack of effect of ivacaftor in CuFi-1 cells. *, p<0.05.
Figure 20C:
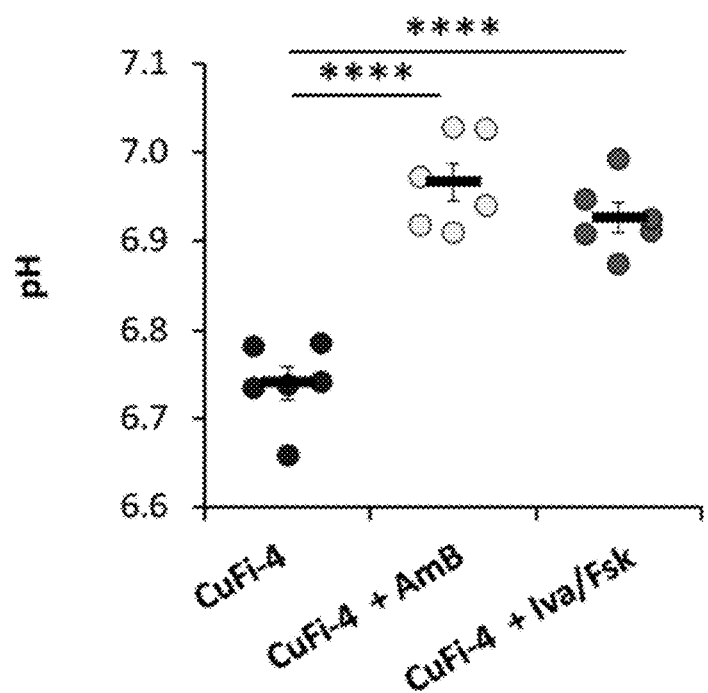
FIG. 20C is a graph depicting the ability of AmB and ivacaftor to increase ASL pH in cystic fibrosis CuFi-4 cells. ****, p<0.0001.

Further connecting the intracellular retention of bicarbonate and pH changes and consistent with the bicarbonate transport findings, treatment with basolateral ouabain inhibited the AmB-mediated increase in ASL pH (FIG. 20A). The genotype-specific ivacaftor/forskolin treatment was unable to increase ASL pH in the CuFi-1 monolayers monolayers, and AmB alone was efficacious in this cell line (FIG. 20B). Importantly, both ivacaftor/forskolin and AmB treatment increased ASL pH in the CuFi-4 epithelia (FIG. 20C). This is a recapitulation of the previous finding that ivacaftor induced a ~0.2 pH unit increase in G551D cultures (E. H. Chang et al., *Int Forum Allergy Rhinol* 5, 178-181 (2015)), and provides evidence that the same pH unit increase mediated by AmB may be clinically significant. Notably, even though AmB replicates only the bicarbonate transport function of CFTR it is able to increase ASL pH as effectively as the ivacaftor-potentiated functional CFTR protein. This implies that simple apical bicarbonate transport may be the most important function of CFTR on lung physiology.

Figure 21:
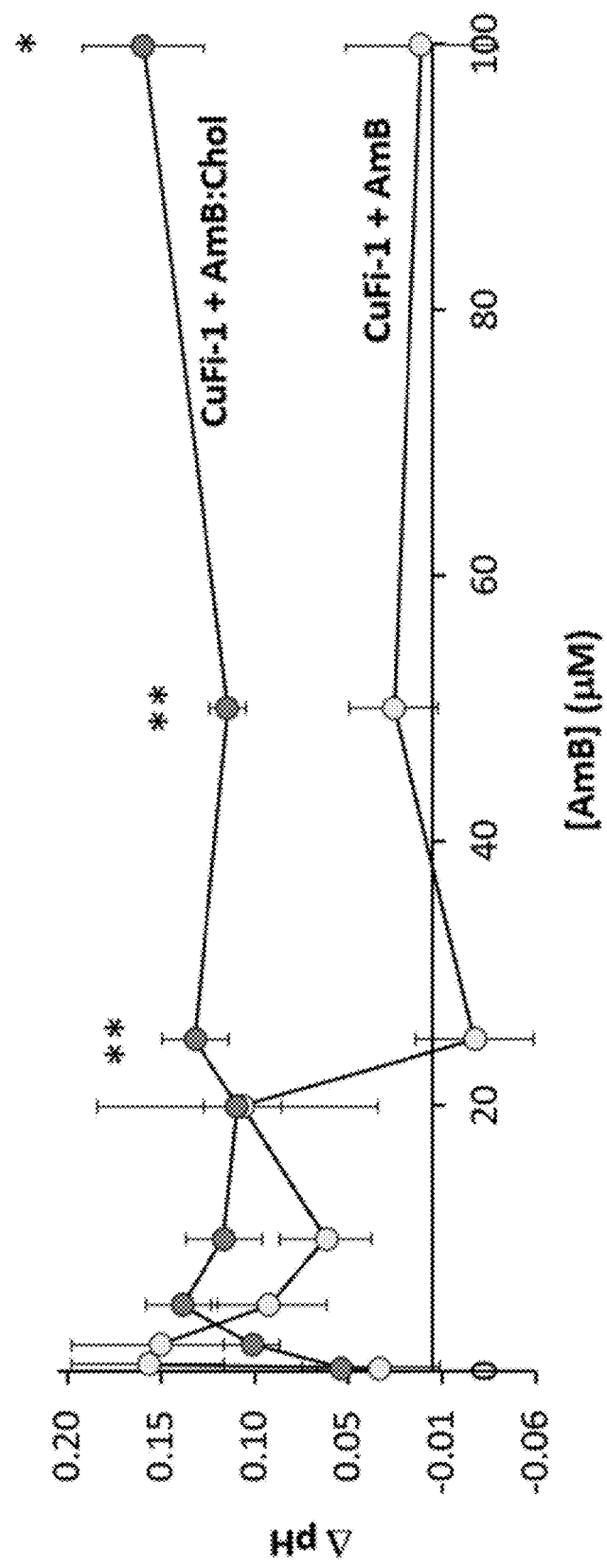
FIG. 21 is a graph depicting dose dependence of change in ASL pH in CuFi-1 cells with pre-formed AmB-cholesterol complexes or AmB alone. *, p<0.05; **, p<0.01.
Figure 22A:
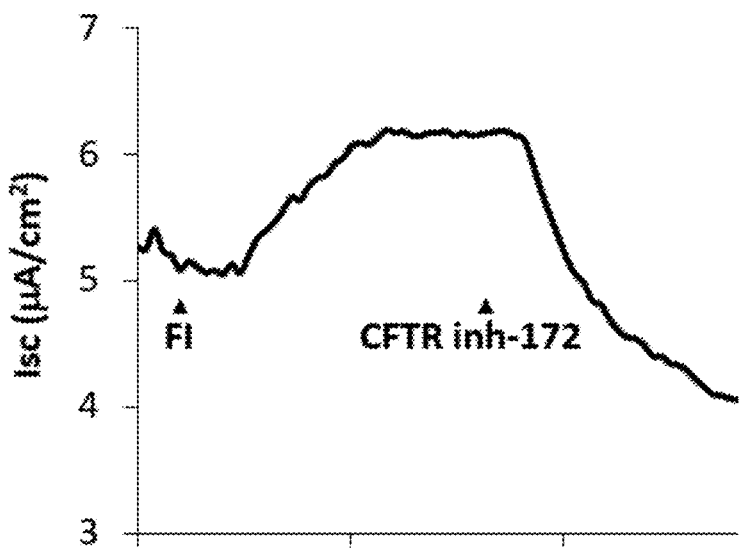
FIG. 22A depicts an Us sing trace of NuLi cells showing an increase in short circuit current in response to forskolin/IBMX CFTR activation.
Figure 22B:
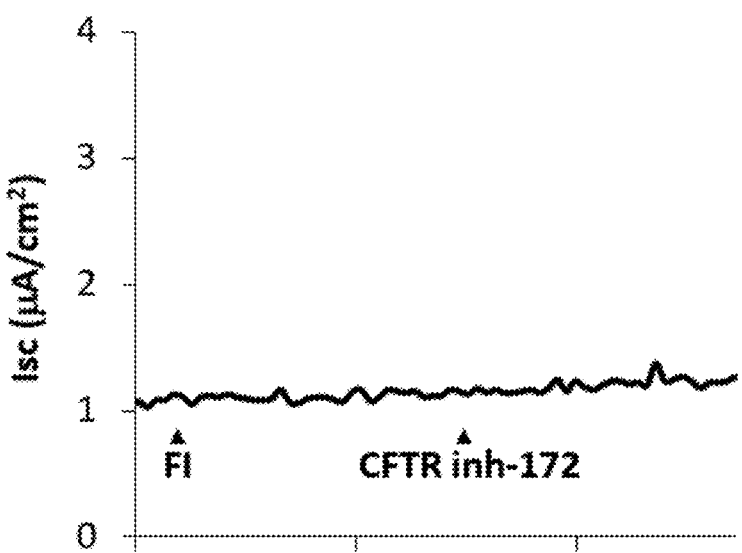
FIG. 22B depicts an Ussing trace of CuFi-1 cells showing no increase in short circuit current in response to forskolin/IBMX CFTR activation.
Figure 22C:
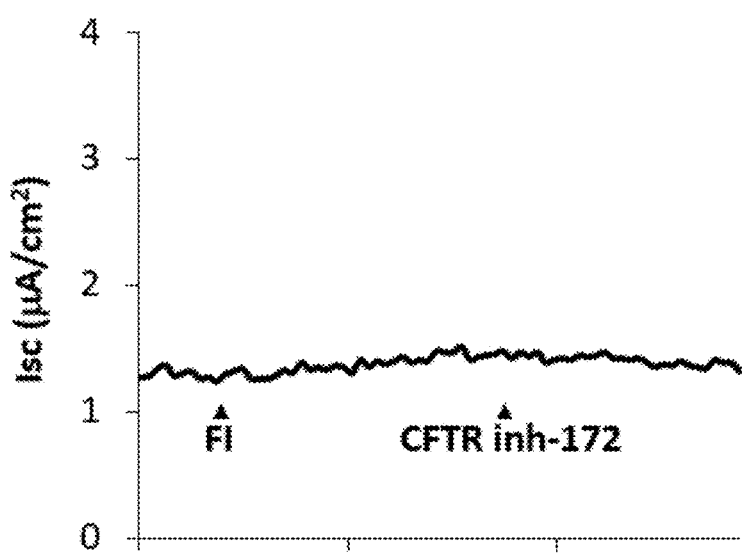
FIG. 22C depicts an Us sing trace of CuFi-1 cells with AmB showing no increase in short circuit current in response to forskolin/IBMX CFTR activation.

Example 14. Pre-Formed Complexes of AmB:Cholesterol Extend the Window of Concentrations Over Which AmB Restores ASL pH in a Bicarbonate-Dependent Manner A range of doses was tested, up to 100 µM suspension in PFC, and it was found that AmB increases ASL pH with dose, peaking at 5 µM suspension in PFC, and then decreasing back down to the starting pH by 25 µM (FIG. 21). After observing this decrease of efficacy with increasing dose, AmB was pre-complexed with cholesterol to mitigate its potentially disruptive sterol binding activity, following the mechanistic model laid out in previous studies. Gray K C et al. (2012) *Proc Natl Acad Sci USA* 109(7): 2234-2239; Anderson T M et al. (2014) *Nat Chem Biol* 10(5): 400-406. The activity of an AmB:cholesterol complex was tested, and this complex was able to extend the effective dose of ASL pH rescue out to 100 μM (FIG. 21). After 48 hr treatment with AmB, CuFi-1 monolayers were evaluated in an Ussing chamber. Compared to NuLi, neither untreated nor AmB-treated CuFi-1 monolayers had an increase in short circuit current in response to forskolin/IBMX CFTR activation, consistent with the conclusion that AmB-mediated increase in ASL pH is not due to increasing CFTR activity/trafficking to the surface or disrupting membrane integrity (FIG. 22A-22C).

Figures 23A, 23B:
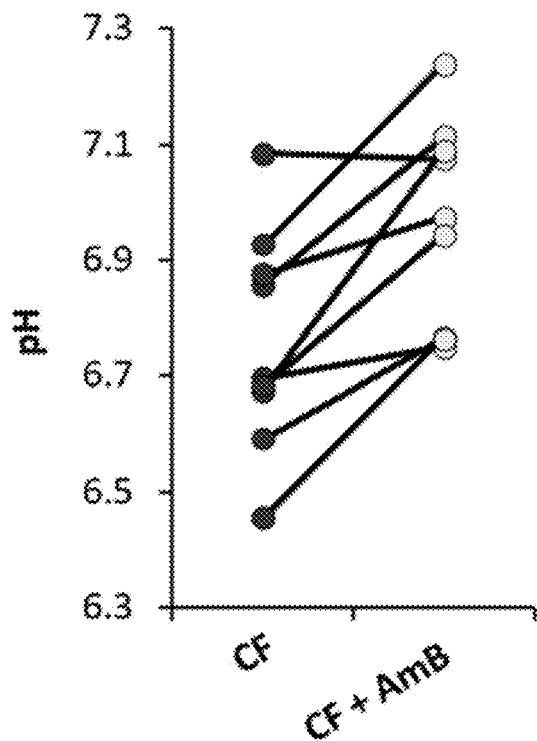
FIG. 23A is a table summarizing the genotype and mutations of samples from cystic fibrosis patients.
FIG. 23B is a graph depicting the ability of AmB to increase ASL pH in CF primary human lung epithelia from patients.

Example 15. AmB Effects on ASL pH in Samples from CF Patients are Genotype-Independent Samples were obtained from CF patient donors, and primary human cell cultures were generated from them in order to determine if observations in cell lines could potentially have clinical relevance. To test ASL pH, CF primary epithelial monolayers were treated with vehicle or AmB. AmB treatment increased ASL pH in primary cultures of human lung epithelia from 9 CF patients with 5 different disease genotypes (FIGS. 23A and 23B). Patients 1-5 had the common ΔF508/ΔF508 mutation. Both patients 8 and 9 have rare, uncategorized mutation alleles, with the latter patient's known second mutation allele in the same category as the ivacaftor target G551D but which was found to be refractory to treatment. AmB was able to promote increase in ASL pH even in the case of a double null mutation genotype (patient 6) or a rare splice site mutation allele (patient 7) that both result in virtually no CFTR protein produced, which provides additional evidence that AmB acts independently from CFTR (FIG. 23B).

Figure 23C:
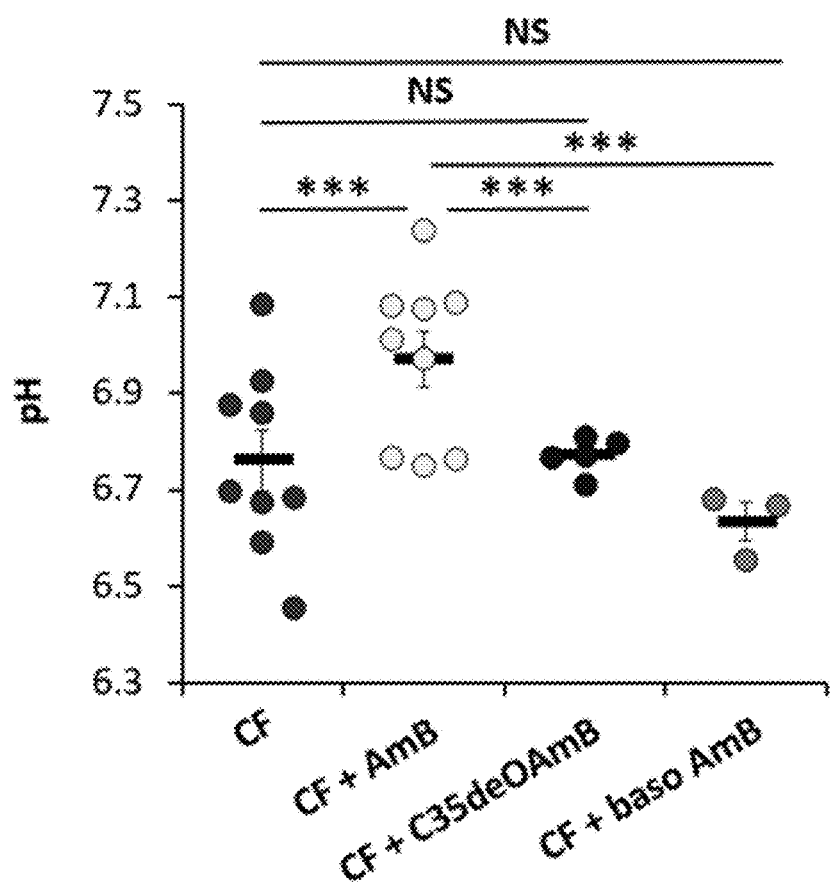
FIG. 23C is a graph depicting the ability of apical, but not basolateral, AmB to increase ASL pH in cystic fibrosis (CF) primary human lung epithelia from patients. The figure also shows the lack of effect of apical C35deOAmB. ***, p<0.001; NS, not statistically significant.
Figure 24A:
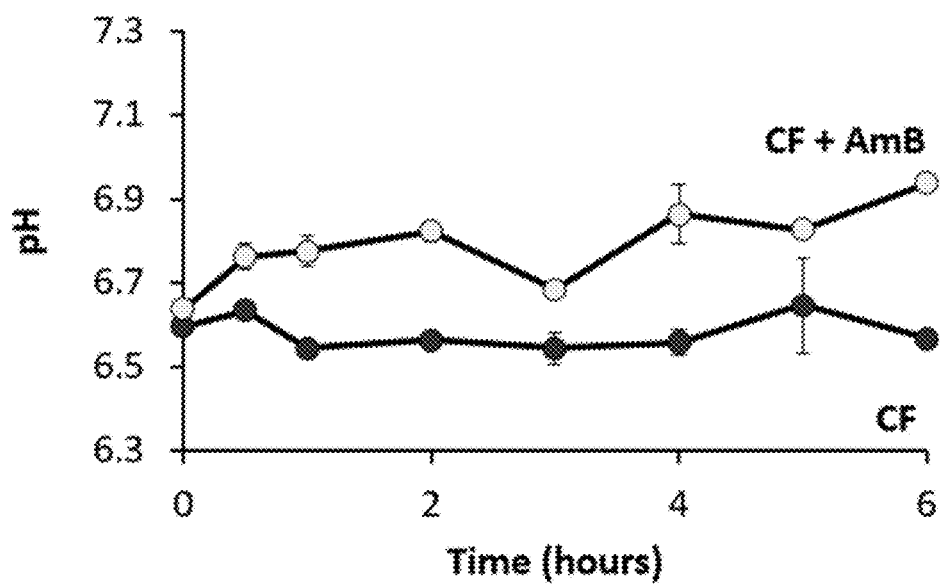
FIG. 24A is a graph depicting the effect of AmB on ASL pH in primary cells over time.
Figure 24B:
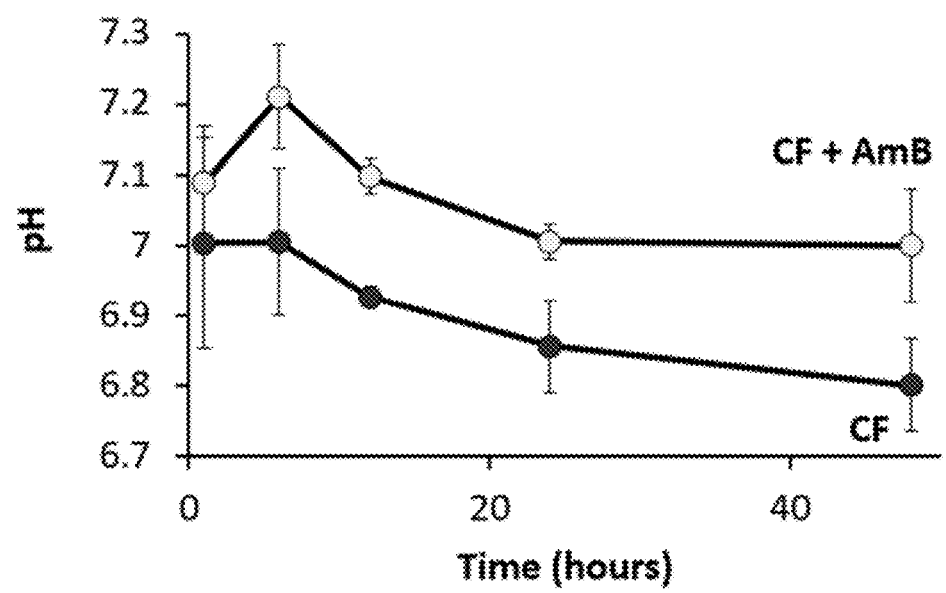
FIG. 24B is a graph depicting the effect of AmB on ASL pH in primary cells over time.
Figure 25:
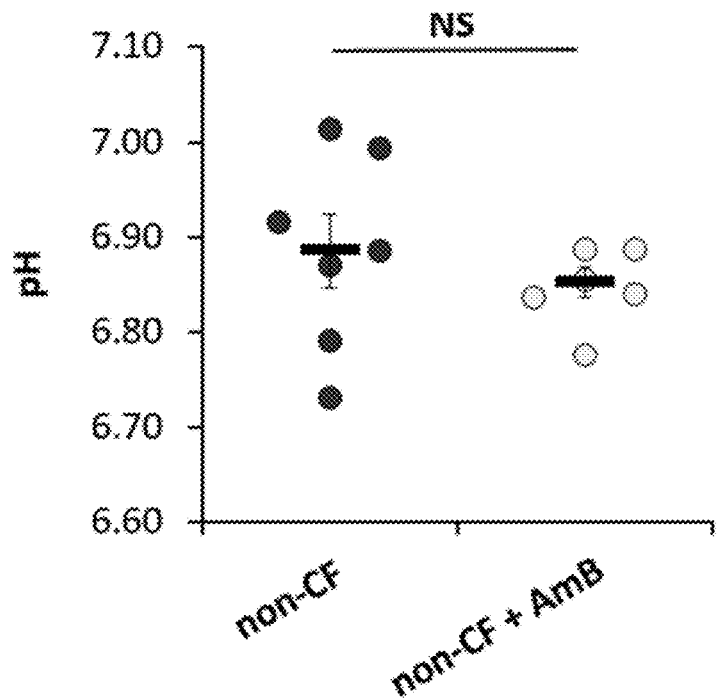
FIG. 25 is a graph depicting the absence of effect of apical AmB on ASL pH of control (non-CF) primary human lung epithelia. NS, not statistically significant.

AmB was found to increase ASL pH in primary human epithelia independent of patient donor genotype by an average of again about 0.2 pH units after 48 hours of apical incubation, while the channel-inactivated derivative C35deOAmB and basolateral addition of AmB were unable to do so, consistent with the findings in the cell line (FIG. 23C). AmB increased pH in primary cells in a dose and time-dependent fashion (FIGS. 24A and 24B). Interestingly, AmB treatment had no effect of the pH of non-CF epithelia, providing further evidence for the necessity of the pooled intracellular bicarbonate for increased apical secretion (FIG. 25).

Example 16. AmB Increases ASL Bacterial Killing in Samples from CF Patients

Figure 26:
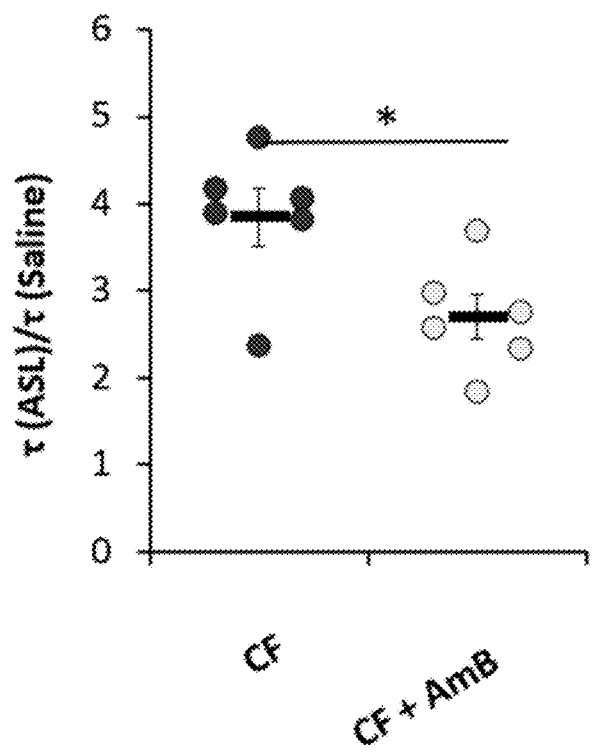
FIG. 26 is a graph depicting that AmB decreases ASL viscosity (t) in CF primary human epithelia independent of patient genotype. *, p<0.05.
Figure 27:
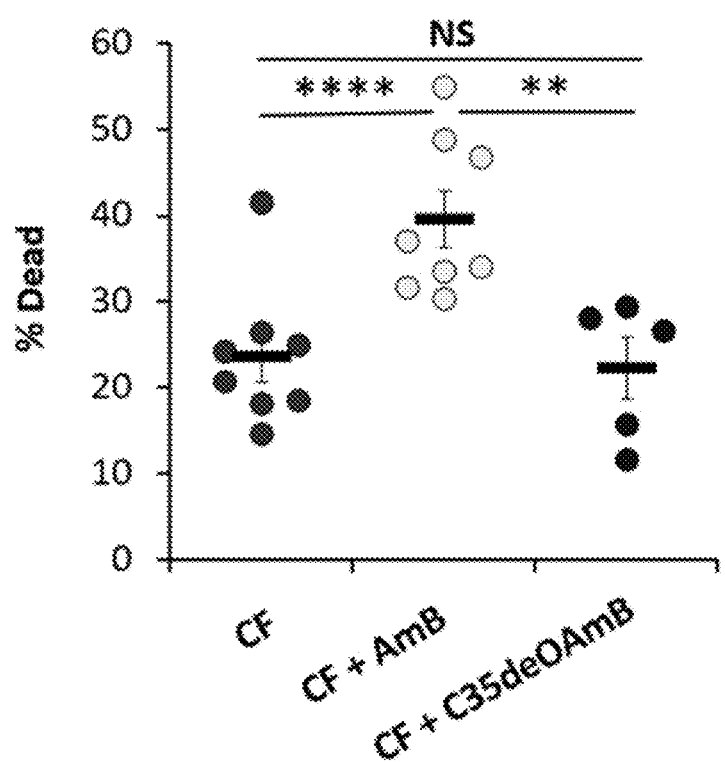
FIG. 27 is a graph depicting that AmB increases ASL bacterial killing in CF primary human epithelia independent of patient genotype. The figure also shows the lack of effect of apical C35deOAmB. , p<0.01; **, p<0.0001; NS, not statistically significant.

Increased ASL viscosity, a downstream effect of ASL pH acidification, contributes to the inability to clear mucus and bacteria from the lung. Consistent with the pH change, AmB decreased ASL viscosity in primary human epithelia independent of patient genotype (FIG. 26). ASL pH is also closely correlated to the ability of antimicrobial proteins in the ASL to enact bacterial killing. To connect the observed AmB-mediated increase in ASL pH with a meaningful increase in ASL bacterial killing, AmB treated epithelia were tested against a human strain of *S. aureus*. Pezzulo A A et al. (2012) *Nature* 487: 109-113. AmB increased ASL bacterial killing in primary human epithelia independent of patient genotype (FIG. 27). Additionally, C35deOAmB was unable to increase ASL antibacterial activity in primary human epithelia, consistent with its inability to increase ASL pH (FIG. 27). These results represent important downstream effects of the AmB-mediated increase in ASL pH that have been observed to be improved by the clinically successful ivacaftor, which may bode well for the potential of AmB as a CF therapeutic.

It is worth noting that AmB acts completely independently of the missing protein and, unlike in more targeted approaches, the underlying mechanism of defect does not need to be known because a fully autonomous approach would work regardless of mutation. Extensive efforts to develop gene therapy approaches, which are in theory generalizable, have been met with substantial scientific challenges and have yet to yield substantial clinical impact. More recently, the combination of ivacaftor and lumacaftor, a corrector of protein misfolding, has shown modest clinical impact in ΔF508/ΔF508 CF patients, specifically showing only a 2-4% improvement in lung function. Wainwright C E et al. (2015) *New Engl. J. Med.* 373, 220-231. Moreover, concerns about the potentially competitive nature of the drugs' mechanisms of action been raised. Cholon D M et al. (2014) *Sci Transl Med* 6, 246ra296. This approach is also fundamentally limited in its capacity to address mutations that cause little to no CFTR protein to be produced, and in the case of rare mutations where the patient population is small and the mechanism of loss-of-function is unknown, it is expected that customized development of a unique drug for each genotype will be difficult to achieve. A line of evidence for the role of ASL pH and downstream effects in the pathophysiology of CF has been presented, pointing to the simple loss of bicarbonate secretion as a major driver for disease.

INCORPORATION BY REFERENCE

All patents and published patent applications mentioned in the description above are incorporated by reference herein in their entirety.

EQUIVALENTS

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

We claim:

1. A method of inhibiting or ameliorating cystic fibrosis, comprising administering to a subject in need thereof a therapeutically effective amount of a composition comprising (i) amphotericin B (AmB), or a pharmaceutically acceptable salt or hydrate thereof, and (ii) cholesterol, thereby inhibiting or ameliorating the cystic fibrosis; wherein the molar ratio of AmB to cholesterol is selected from the range from 1:2.6 to about 1:50; the composition is in the form of a dry powder; and the composition is administered to the subject by inhalation.

2. The method of claim 1, wherein the AmB and the cholesterol are present in a molar ratio in the range from about 1:3 to about 1:15.

3. The method of claim 1, wherein the AmB and the cholesterol are present in a molar ratio in the range from about 1:4 to about 1:12.

4. The method of claim 2, wherein the AmB and the cholesterol are present in a molar ratio in the range from about 1:5 to about 1:10.

5. The method of claim 1, wherein the composition is administered an airway of the subject.

6. A method of increasing the pH of airway surface liquid in a subject having cystic fibrosis, comprising administering to the subject having cystic fibrosis a therapeutically effective amount of a composition comprising (i) amphotericin B (AmB), or a pharmaceutically acceptable salt or hydrate thereof, and (ii) cholesterol, thereby increasing the pH of airway surface liquid in the subject having cystic fibrosis; wherein the molar ratio of AmB to cholesterol is selected from the range from 1:2.6 to about 1:50; the composition is in the form of a dry powder; and the composition is administered by inhalation.

7. The method of claim 6, wherein the AmB and the cholesterol are present in a molar ratio in the range from about 1:3 to about 1:15.

8. The method of claim 6, wherein the AmB and the cholesterol are present in a molar ratio in the range from about 1:4 to about 1:12.

9. The method of claim 6, wherein the AmB and the cholesterol are present in a molar ratio in the range from about 1:5 to about 1:10.

10. The method of claim 6, wherein the composition is administered to an airway of the subject.

11. The method of claim 1, wherein the cystic fibrosis genotype is selected from the group consisting of ΔF508/ΔF508, R553X/E60X, ΔF508/1717-1G→A, ΔF508/c.2052dupA, D293G/V520F, and G551D.

12. The method of claim 1, wherein the cystic fibrosis is refractory.

13. The method of claim 1, wherein the cystic fibrosis genotype is selected from the group consisting of ΔF508/ΔF508, R553X/E60X, ΔF508/1717-1G→A, ΔF508/c.2052dupA, D293G/V520F, and G551D; and the cystic fibrosis is refractory.

14. The method of claim 6, wherein the cystic fibrosis genotype is selected from the group consisting of ΔF508/ΔF508, R553X/E60X, ΔF508/1717-1G→A, ΔF508/c.2052dupA, D293G/V520F, and G551D.

15. The method of claim 6, wherein the cystic fibrosis is refractory.

16. The method of claim 6, wherein the cystic fibrosis genotype is selected from the group consisting of ΔF508/ΔF508, R553X/E60X, ΔF508/1717-1G→A, ΔF508/c.2052dupA, D293G/V520F, and G551D; and the cystic fibrosis is refractory.

* * * * *

UNITED STATES PATENT AND TRADEMARK OFFICE
CERTIFICATE OF CORRECTION

| | | |
|---|---|---|
| PATENT NO. | : 11,850,256 B2 | Page 1 of 1 |
| APPLICATION NO. | : 17/335803 | |
| DATED | : December 26, 2023 | |
| INVENTOR(S) | : Martin D. Burke et al. | |

It is certified that error appears in the above-identified patent and that said Letters Patent is hereby corrected as shown below:

In the Claims

At Column 57, Claim number 5, Line number 8, please delete:
"administered an airway of the subject"

And replace with:
-- administered to an airway of the subject --

Signed and Sealed this
Eighth Day of April, 2025

Coke Morgan Stewart
*Acting Director of the United States Patent and Trademark Office*